(12) United States Patent
Wiederin et al.

(10) Patent No.: US 7,637,175 B1
(45) Date of Patent: Dec. 29, 2009

(54) AUTOMATED SAMPLING DEVICE

(75) Inventors: Daniel R. Wiederin, Omaha, NE (US); David Diaz, Omaha, NE (US); Gary Barrett, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 388 days.

(21) Appl. No.: 11/590,305

(22) Filed: Oct. 31, 2006

Related U.S. Application Data

(63) Continuation-in-part of application No. 10/966,888, filed on Oct. 15, 2004, now Pat. No. 7,201,072.

(60) Provisional application No. 60/604,548, filed on Aug. 26, 2004.

(51) Int. Cl.
*G01N 1/00* (2006.01)

(52) U.S. Cl. .................................. 73/864.25

(58) Field of Classification Search ........................ None
See application file for complete search history.

(56) References Cited

U.S. PATENT DOCUMENTS

| | | | |
|---|---|---|---|
| 3,022,718 A | 2/1962 | Thompson | |
| 4,529,403 A * | 7/1985 | Kamstra | 604/136 |
| 4,767,413 A * | 8/1988 | Haber et al. | 604/198 |
| 4,822,340 A * | 4/1989 | Kamstra | 604/135 |
| 4,888,998 A * | 12/1989 | Buzza et al. | 73/864.21 |
| 4,926,746 A | 5/1990 | Smith | |
| 5,270,211 A | 12/1993 | Kelln et al. | 436/43 |
| 5,331,840 A | 7/1994 | Williams | 73/19.1 |
| 5,364,596 A * | 11/1994 | Magnussen et al. | 422/100 |
| 5,464,029 A | 11/1995 | Rentz | |
| 5,479,969 A | 1/1996 | Hardie et al. | 141/130 |
| 5,527,296 A * | 6/1996 | Kashanchi | 604/263 |
| 5,876,668 A | 3/1999 | Kawashima et al. | 422/64 |
| 5,879,944 A | 3/1999 | Komatsu | 436/50 |
| 6,001,309 A | 12/1999 | Gamble et al. | 422/100 |
| 6,148,680 A * | 11/2000 | Baeuerle et al. | 73/864.25 |
| 6,203,760 B1 | 3/2001 | van der Plaats et al. | 422/104 |
| 6,595,247 B1 | 7/2003 | Landy et al. | |
| 6,637,476 B2 | 10/2003 | Massaro | 141/237 |
| 2002/0106814 A1 | 8/2002 | Matsubarg et al. | 436/180 |
| 2003/0077203 A1 | 4/2003 | Gudmundsson et al. | 422/67 |
| 2003/0090174 A1 | 5/2003 | Ryder | |
| 2003/0143748 A1 | 7/2003 | Gudmundsson et al. | 436/43 |
| 2003/0143749 A1 | 7/2003 | Gudmundsson et al. | 436/43 |
| 2003/0147778 A1 | 8/2003 | Takahashi | 422/63 |
| 2003/0180188 A1 | 9/2003 | Michael et al. | 422/99 |
| 2004/0018119 A1 | 1/2004 | Massaro | 422/100 |
| 2004/0126283 A1 | 7/2004 | Backes et al. | 422/104 |
| 2004/0146433 A1 | 7/2004 | Massaro | 422/100 |
| 2005/0095724 A1 | 5/2005 | Shibutani et al. | 436/180 |
| 2006/0074349 A1* | 4/2006 | Fan | 600/576 |
| 2006/0088940 A1 | 4/2006 | Feingold et al. | 436/47 |
| 2006/0120922 A1 | 6/2006 | Matsumoto | 422/64 |

* cited by examiner

*Primary Examiner*—Robert R Raevis
(74) *Attorney, Agent, or Firm*—Suiter Swantz pc llo

(57) ABSTRACT

A dampening device for an automated sampling/dispensing device. In an exemplary embodiment, the dampening device includes a cylindrical body. The cylindrical body includes a first end and a second end, a first opening being defined within the first end and a second opening being defined within the second end. Further, the cylindrical body may include an inner diameter greater than an outer diameter of an automated sampling/dispensing device sample probe. During operation, the dampening device moves out of phase with the automated sampling/dispensing device sample probe allowing sample probe vibrations to be dampened during operation.

13 Claims, 24 Drawing Sheets

AUTOMATED SAMPLING DEVICE

CROSS REFERENCE

The present application is a continuation-in-part under 35 U.S.C. § 120 of U.S. patent application Ser. No. 10/966,888 filed Oct. 15, 2004 now U.S. Pat. No. 7,201,072 which in turn claims the benefit under 35 U.S.C. § 119(e) of U.S. Provisional Application Ser. No. 60/604,548, filed Aug. 26, 2004 both of which are herein incorporated by reference in their entirety.

FIELD OF INVENTION

The present invention relates generally to laboratory instrumentation, particularly automated sampling devices for drawing samples from stationary sample vessels, and more specifically, to a dampening device for an automated sampling/dispensing device.

BACKGROUND OF THE INVENTION

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

While a vast array of autosamplers are currently known and available, the majority of such devices share one common feature, employing robotic-like systems to analyze multiple vessels or containers containing samples in a given time. Many such devices are equipped with a robotic manipulator capable of two types of linear movement, i.e., x-y and vertical which allows the manipulator to access a container, transfer the container from a parent machine, and return the container to the appropriate position in the sample tray. Another common style of autosampler is one which employs robotic movement to move a sample probe above a sample vessel, or, alternatively, employs a moving table or conveyer to move the sample vessels underneath the sample probe.

Although autosamplers presently known in the art have greatly increased the ease and efficiency of assaying multiple samples at a given time, such samplers are disadvantageous in that they are likely to introduce an additional source for sample contamination, allowing for contamination of sample vessels by contaminants which may fall into containers during analysis. Present autosamplers employing mechanical parts may cause dust, or the like, to fall into these containers because of mechanical wear of the devices that either is directly above the containers while they are moving or as the containers themselves move underneath a dispensing pipette. Further, such autosamplers are typically not enclosed exposing the samples to particulates and other matter present in the air. In addition, prior art autosamplers often result in sample loss or sample cross-contamination during assaying due to the sample probe of the autosampler moving rapidly and vibrations associated with such rapid movement.

What is desired, therefore, is an automated sampling device without any mechanical moving parts positioned above stationary samples thereby removing such possible source of contamination. Further, it is desired that the automated sampling device be protected from the external environment by placing the device in an automated sampling device enclosure. Moreover, a mechanism which allows an autosampler to move rapidly from sample to sample without affecting sample volume or causing sample cross-contamination is also desired.

SUMMARY OF INVENTION

Accordingly, the present invention is directed to a dampening device. In accordance with a first aspect of the present invention, a dampening device for an automated sampling/dispensing device is disclosed. In an exemplary aspect, the dampening device includes a cylindrical body. The cylindrical body includes a first end and a second end, a first opening being defined within the first end and a second opening being defined within the second end. Further, the cylindrical body may include an inner diameter greater than an outer diameter of an automated sampling/dispensing device sample probe. During operation, the dampening device moves out of phase with the automated sampling/dispensing device sample probe allowing sample probe vibrations to be dampened during operation.

In accordance with a further aspect of the present invention, a dampening device for an automated sampling/dispensing device is provided. In an exemplary aspect, the dampening device includes a body. The body may include a plurality of walls, a first end and a second end. Further, a first opening is defined within the first end and a second opening is defined within the second end for allowing the body to be positioned around an automated sampling/dispensing device sample probe. Additionally, the body includes an inner diameter greater than an outer diameter of the automated sampling/dispensing device sample probe. The dampening device is positioned around the automated sampling/dispensing device sample probe so that during operation the device moves out of phase with the automated sampling/dispensing device sample probe allowing sample probe vibrations to be dampened.

In accordance with an additional aspect of the present invention, an automated sampling/dispensing device including a dampening device is provided. In such aspect, the automated sampling/dispensing device includes a support surface for supporting a sample holder. The sample holder is suitable for holding a sample vessel. Further, a sample arm assembly for supporting a sample probe is included in which such assembly includes a z-axis support and a sample probe support arm. Additionally, a drive assembly is coupled to the z-axis support of the sample arm assembly for powering and positioning the sample arm assembly so that the drive assembly causes the sample arm assembly to move in translation along the x-axis, in translation along an axis coaxial with the z-axis support, and radially about the z-axis. Moreover, a dampening device is operationally coupled to the sample arm assembly for dampening vibrations of the sample arm assembly during operation. The dampening device includes a cylindrical body. The cylindrical body includes a first end and a second end with a first opening being defined within the first end and a second opening being defined within the second end for allowing the cylindrical body to be positioned around the sample probe. In addition, the cylindrical body includes an inner diameter greater than an outer diameter of the sample probe. The dampening device is positioned around the sample probe so that during operation the dampening device moves out of phase with the sample probe allowing sample probe vibrations to be dampened.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles of the invention.

BRIEF DESCRIPTION OF DRAWINGS

The numerous objects and advantages of the present invention may be better understood by those skilled in the art by reference to the accompanying figures in which.

DETAILED DESCRIPTION OF INVENTION

Reference will now be made in detail to the presently preferred embodiments of the invention, examples of which are illustrated in the accompanying drawings.

Figure 1:
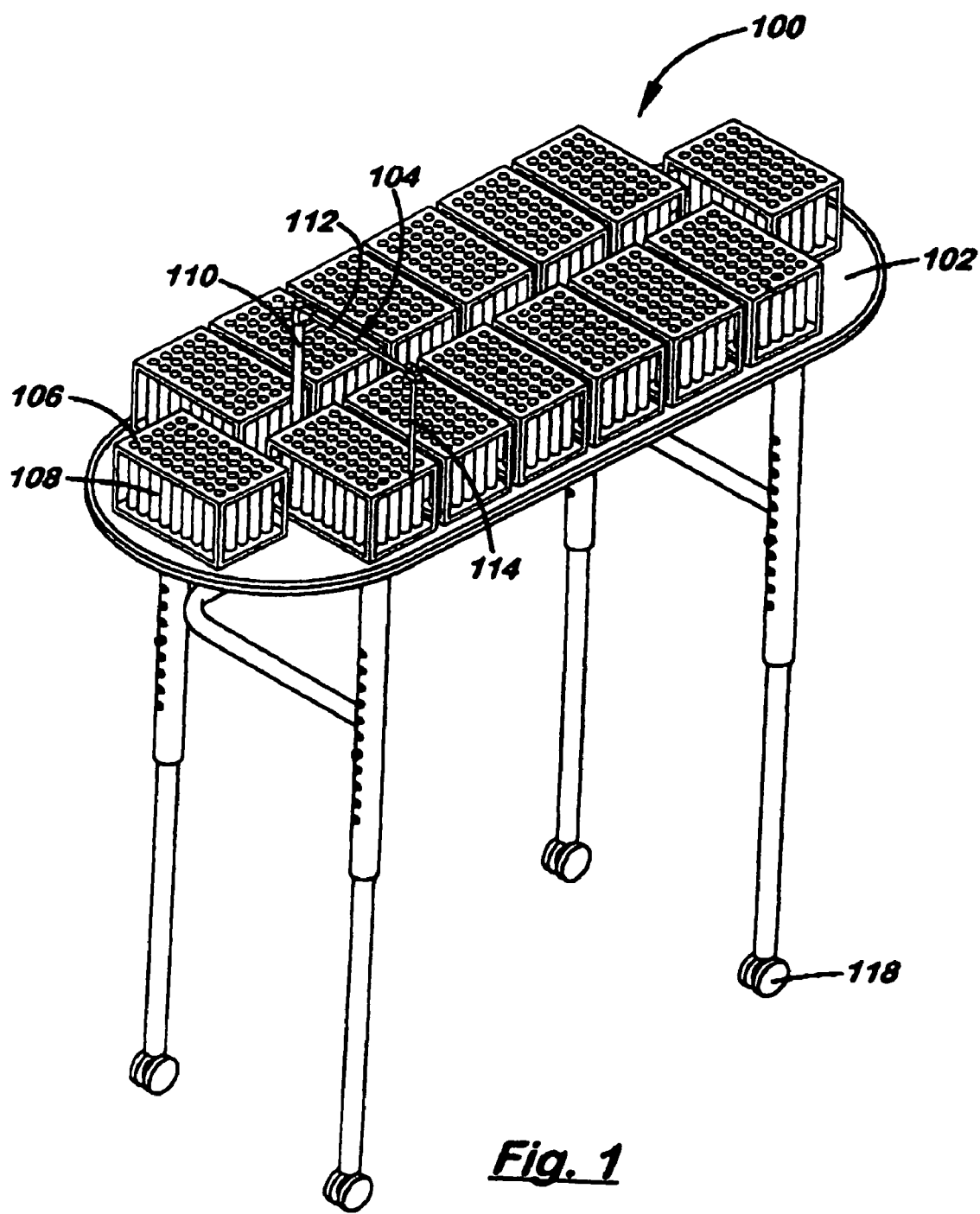
FIG. 1 is an isometric view illustrating an automated sampling or dispensing device in accordance with an exemplary embodiment of the present invention.

FIG. 1 illustrates automated sampling device 100 in accordance with an exemplary embodiment of the present invention. Automated sampling device 100 includes table top 102 and sample arm assembly 104. Further, sample holders 106 holding multiple sample vessels 108 are present on table top 102 in preparation for sample assaying. It should be understood that automated sampling device 100 may assay from one to many hundreds of samples (e.g., greater than 1200 samples in the exemplary embodiment illustrated) in a given time depending upon test requirements.

In the embodiment illustrated, sample arm assembly 104 includes a z-axis support 110 and a sample probe support arm 112 that supports a sample probe 114. As illustrated, the z-axis which is aligned with gravity or vertical axis. In use, sample probe 114 is mounted to sample probe support arm 112 which is moved through space in three dimensions, or about an axis having y-motion that is a substantially rotary motion and along an axis having x-motion which is at least substantially horizontal linear motion or translation, and along a z-axis that is at least substantially vertical, for linear motion or translation. In an embodiment, the length of a sample probe support arm (the length of arm extending from the y-rotary axis) is no more than one-half the length of a linear translation of the center slot (i.e. is no more than half of the length of x-axis linear motion). In a preferred embodiment, the length of the sample probe support arm is approximately equal to one-half the length of a linear translation of the center slot. Such configuration allows nearly one hundred percent of the footprint of the table to be accessed by the sample probe. Footprint is defined as being substantially equivalent to an area encompassed by the area of the table top. In an additional embodiment, the y-rotary axis of an automated sampling device allows for access to sample vessels on either side of the x-axis motion of linear travel (i.e. on either side of the center slot).

In an embodiment, the components of sample arm assembly 104 are formed of carbon composite materials. Further, all exposed surfaces of the sample arm assembly 104 are made from inert or fluoropolymer-covered materials (i.e. Teflon®). It should be understood, however, that the sample arm assembly may be made with any suitable material known in the art, including aluminum, steel, plastic, and the like.

In addition, sample arm assembly 104 is designed to attach to any type of surface support including a table top. Such assembly may be attached to either side of the center slot. In an embodiment, table top 102 may be mounted onto legs with casters 118, rollers and the like. Such configuration increases the mobility of the automated sampling device, thereby facilitating preparation of samples at a location separate from the analytical instruments. Further, this configuration provides storage room underneath the table top which may be absent with bench-top automated sampling devices. The height of the table is adjustable to compensate for the effects of gravity on liquid flow rates when self-aspirating sampling devices are utilized. The ability to adjust table top height also allows the automated sampling device to accommodate various sized sample vessels.

Figure 2A:
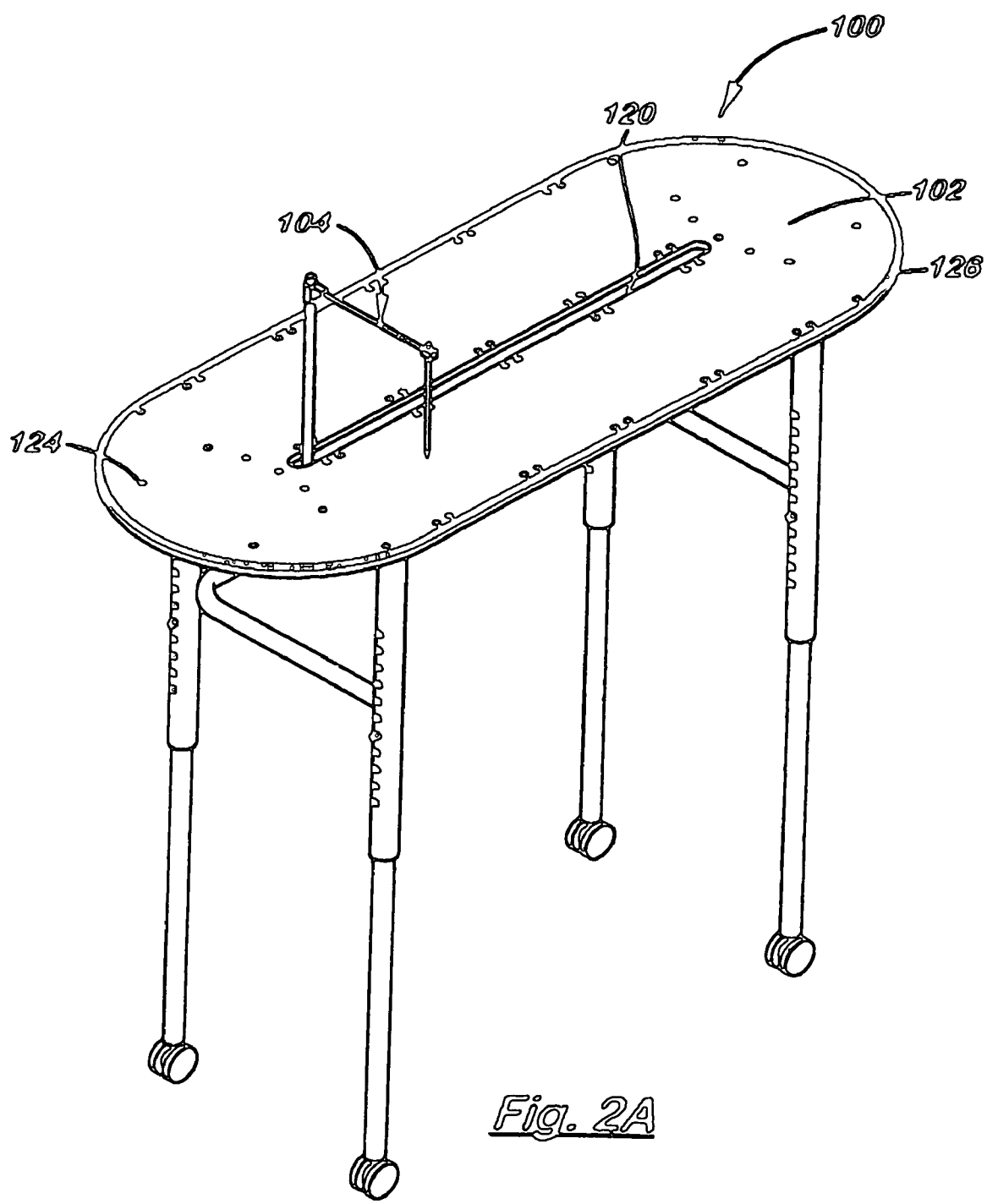
FIG. 2A is a partial isometric view of an automated sampling or dispensing device, wherein a center slot in the support surface is present allowing the sample arm assembly to be connected with the drive assembly.
Figure 2B:
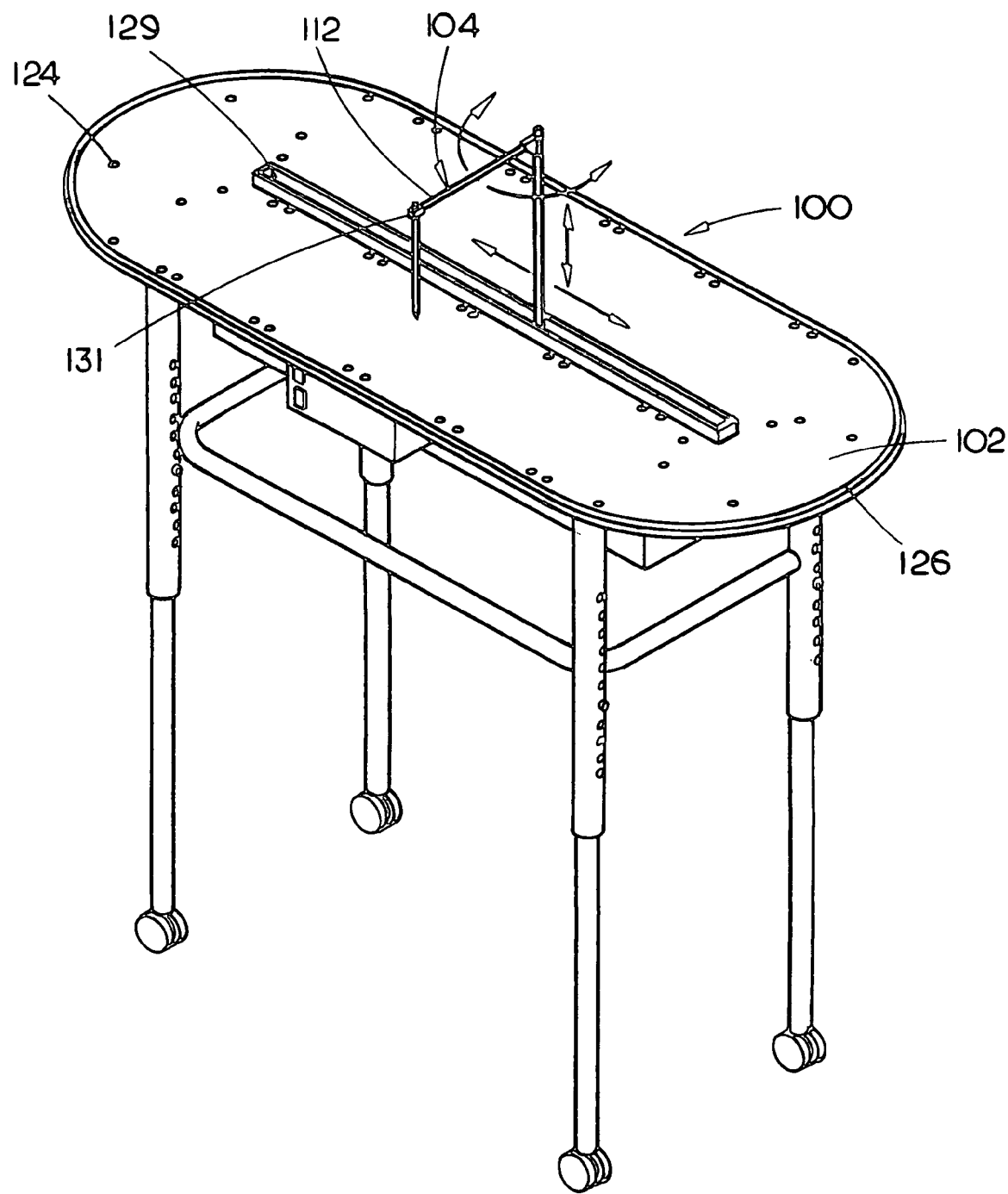
FIG. 2B is a partial isometric view of an automated sampling or dispensing device, wherein a raised slot on the support surface is present to attach the sample arm assembly to the drive assembly.

FIGS. 2A and 2B are additional illustrations of automated sampling or dispensing devices in which the sample arm assembly is attached to the drive assembly via a center slot or a raised slot, respectively. In FIG. 2A, automated sampling device 100 is comprised of sample arm assembly 104 extending through center slot 120 and table top 102 including a plurality of recesses 124 and the channel 126. The sample arm assembly 104 is attached to the drive assembly (not shown) via center slot 120. In an embodiment, the plurality of recesses is coupled with sensors for detecting the location of sample holders. The sample holder location information may then be transferred to a controller of a drive assembly controlling the sample arm assembly providing the alignment system. The previous configuration allows the sample arm assembly to detect the location of sample vessels on the table top at a given time. Channel 126 runs along the edge of table top 102 to collect possible sample spillage.

In addition to FIG. 2A, FIG. 2B demonstrates an automated sampling or dispensing device including a sample arm assembly 104 attached to the drive assembly 128 via a raised slot 129. In one embodiment, a magnet 131 is attached to the end of the sample probe support arm 112 which allows detection of a three-dimensional position in space wherein the magnet 131 is embedded into the sample probe support arm 112 and is detected by a sensing means such as a Hall Effect sensor.

Figure 3:
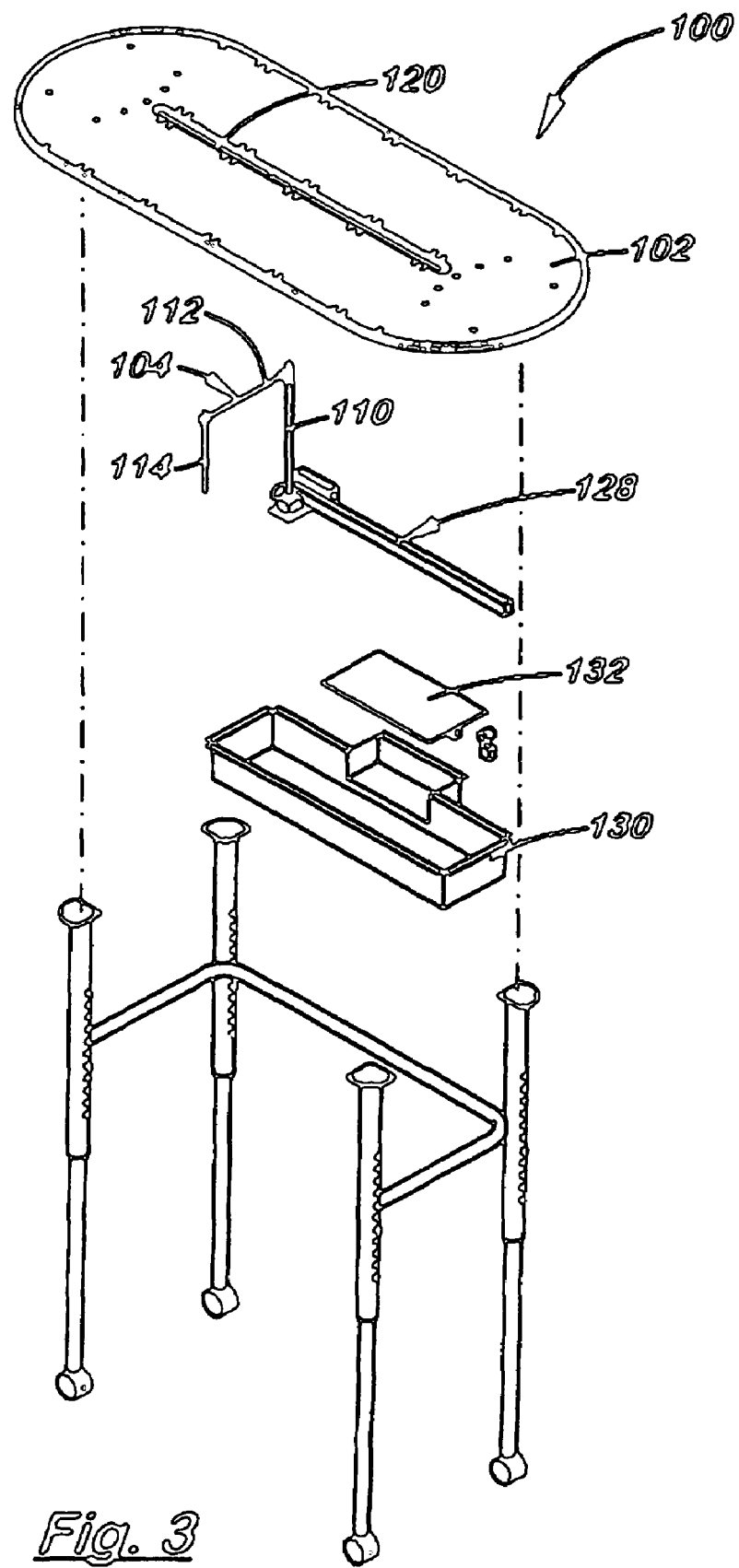
FIG. 3 is an exploded view of the automated sampling or dispensing device shown in FIG. 1, further illustrating components of the device.

Referring now to FIG. 3, an exploded view of the components comprising the automated sampling device 100 is provided. The automated sampling device 100 is comprised of a table top 102 with center slot 120, drive assembly 128, sample arm assembly 104, housing 130, and controller 132. Sample arm assembly 104 includes z-axis support 110 attached to drive assembly 128, sample probe support arm 112 attached to z-axis support 110, and sample probe 114 attached to sample probe support arm 112. Sample arm assembly 104 is controlled by drive assembly 128 and controller 132. In an embodiment, drive assembly 128 causes sample arm assembly 104 to move along center slot 120, in translation along an axis coaxial to z-axis support 110, and radially about the z-axis for inserting sample probe 114 into a sample vessel. Further, sample arm assembly 104 is no more than one-half the length of a linear translation of the length of center slot 120. As previously mentioned, such configuration allows nearly one hundred percent of the footprint to be accessed by sample probe 114. In addition, automated sampling device 100 is capable of assaying hundreds of samples at a given time without any operator assistance, thereby allowing the operator to perform other tasks. Moreover, it is possible to set-up the automated sampling device to assay samples overnight, allowing work productivity to be increased.

To accommodate gross differences in sample vessel height, sample probe support arm 112 may be moved up or down z-axis support 110 as desired prior to sample assaying. Once the desired position is reached, sample probe support arm 112 is secured into a fixed position on z-axis support 110 and sample vessels containing samples may be loaded onto the table top. This feature allows the automated sampling device to be used on various sizes of sample vessels while still not having any mechanical moving parts above stationary samples. Additionally, housing 130 encloses drive assembly 128 to protect the assembly from debris, dust, contaminates, and the like. Housing 130 may be made of any suitable material, e.g. blow molded polyethylene.

Figure 4A:
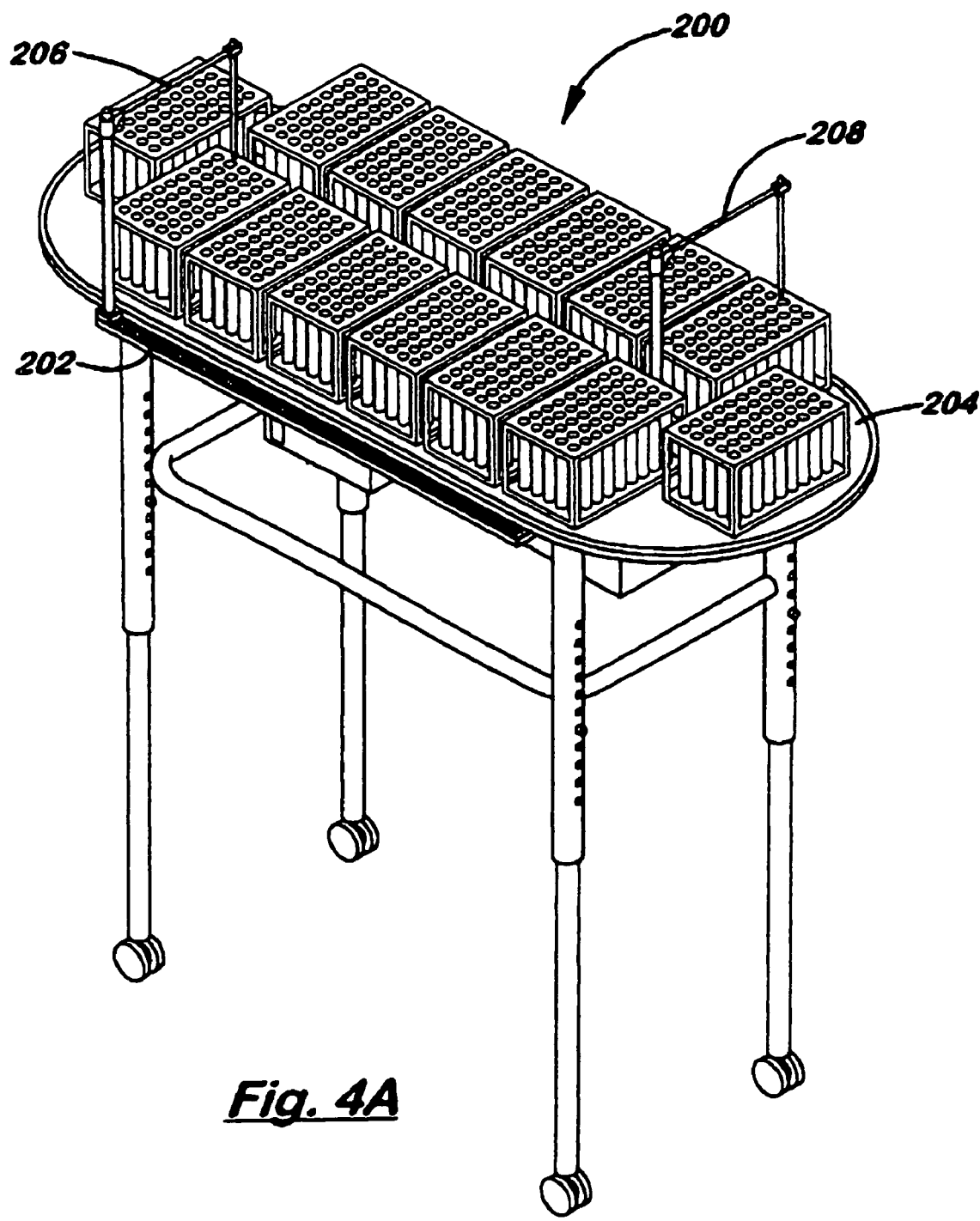
FIG. 4A is an isometric view illustrating an automated sampling or dispensing device in accordance with a second exemplary embodiment of the present invention wherein multiple sampling arm assemblies and drive assemblies are mounted to the top of the support surface of the automated sampling or dispensing device.
Figure 4B:
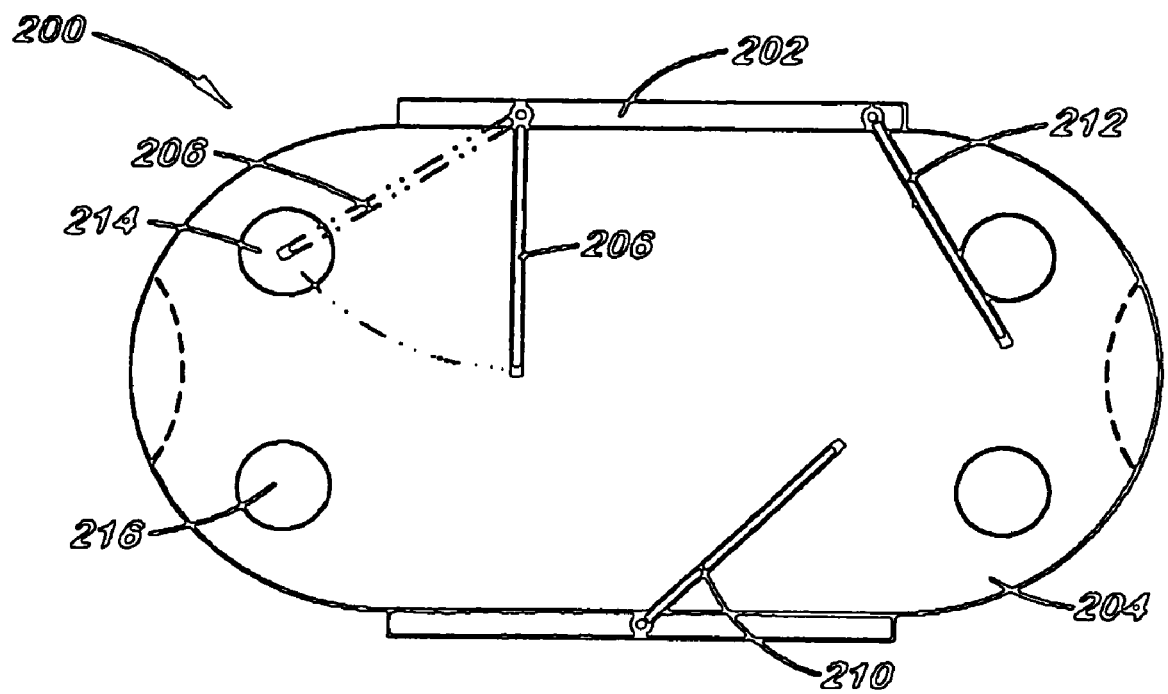
FIG. 4B is plan view illustrating an automated sampling or dispensing device in accordance with the second exemplary embodiment of the present invention, wherein multiple sample arm assemblies and rinse stations are present on one support surface.

FIGS. 4A and 4B illustrate an automated sampling device 200 in accordance with a second exemplary embodiment of the present invention wherein multiple sampling arm assemblies (i.e. sample arm assembly 206, 208, and 210) are mounted to the table top of the automated sampling device. Automated sampling device 200 includes multiple automated sampling devices attached to a table top at one time. A rail 202 is attached to the edge of table top 204 to enable the attachment of additional sample arm assemblies (i.e. sample arm assembly 206 and 212). Utilization of additional sample arm assemblies allows multiple sample zones to be set up (i.e. prep zone, assaying zone, and the like).

In additional embodiments, various types of multiple rinse or eluent stations may be included in the automated sampling device. For instance, multiple rinse stations (i.e. 214 and 216) of the overflow type designed to reduce the chance of carry-over contamination may be present. Further, overflow rinse stations may contain a series of different chemical rinses to reduce contamination between sample analyses (e.g. surfactant, nitric acid, hydrofluoric acid, and deionized water). For multiple eluent stations, the automated sampling device may contain such stations for step elution from a chromatographic column.

Figure 5:
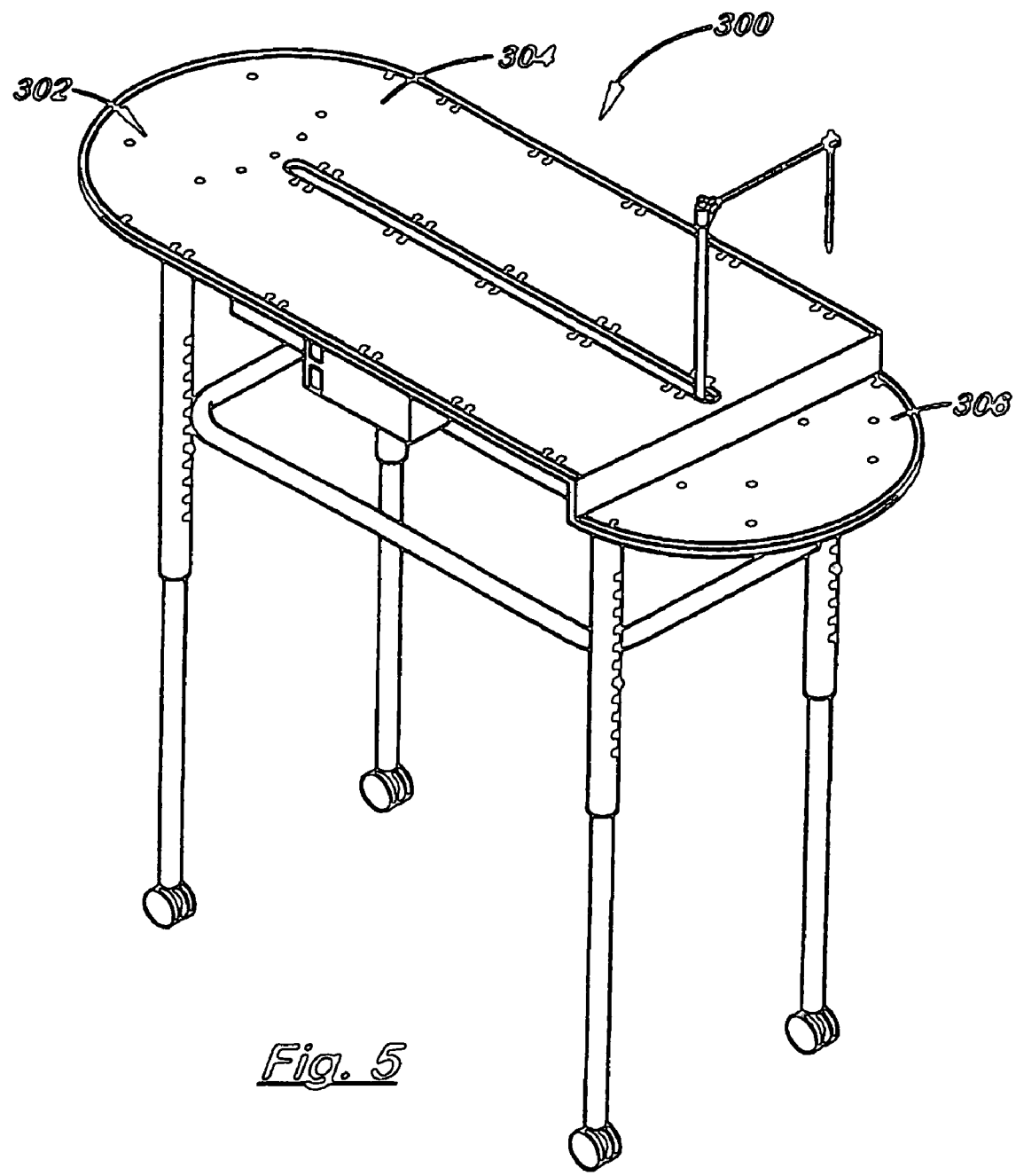
FIG. 5 is an isometric view illustrating an automated sampling or dispensing device in accordance with a third exemplary embodiment of the present invention, wherein the support surface of the automatic sampling or dispensing device is provided with more than one plane.

Referring now to FIG. 5, an automated sampling device in accordance with a third exemplary embodiment of the present invention is disclosed wherein a table top having more than one plane is provided. Automated sampling device 300 includes table top 302 which has more than one plane, plane one 304 and plane two 306. Such configuration allows table top 302 to accommodate various sizes of vessels. For instance, the height of vessels in plane two 306 may be taller than vessels in plane one 304 of table top 302.

Figure 6:
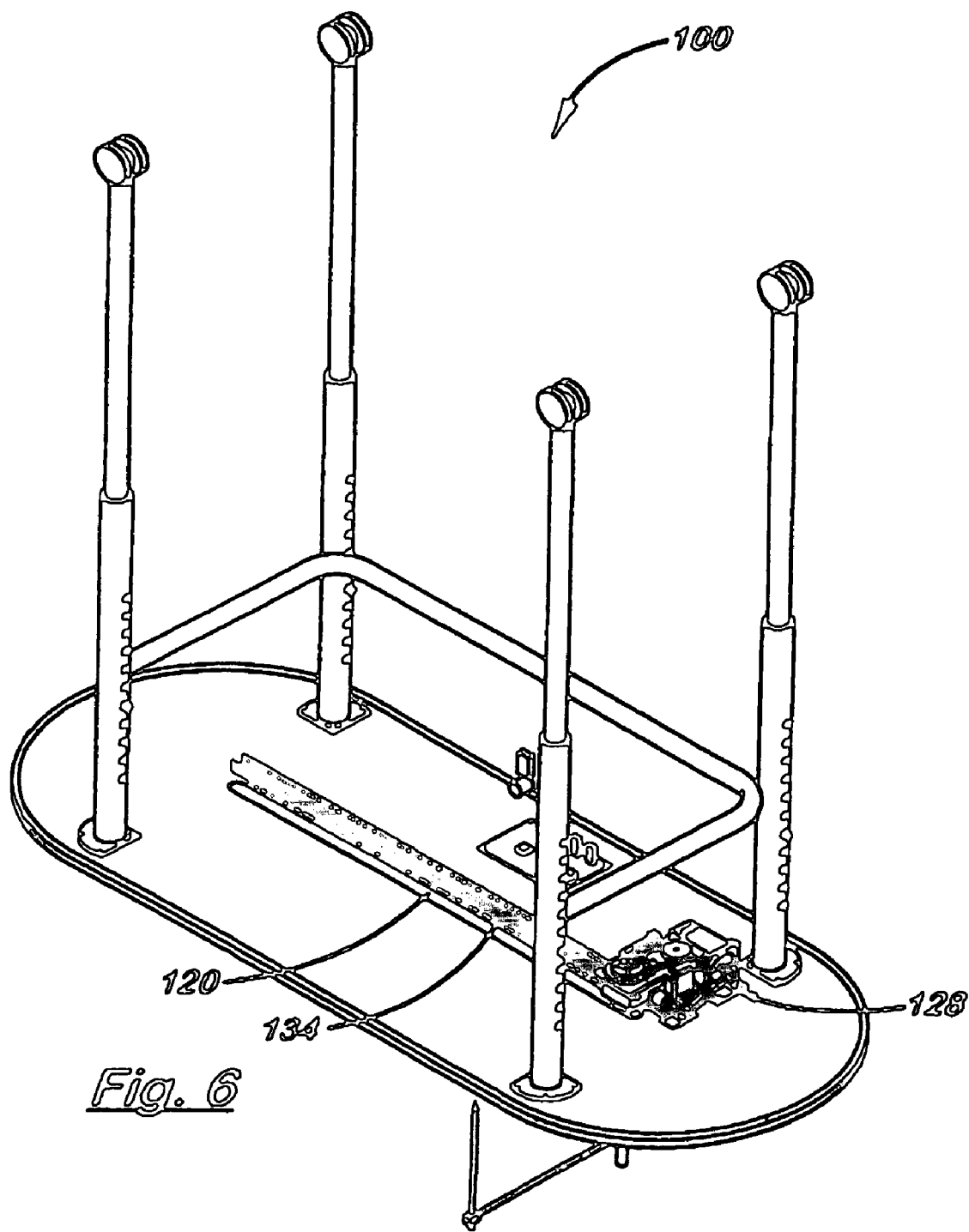
FIG. 6 is an isometric view of the automated sampling or dispensing device shown in FIG. 1, further illustrating the drive assembly.
Figure 7:
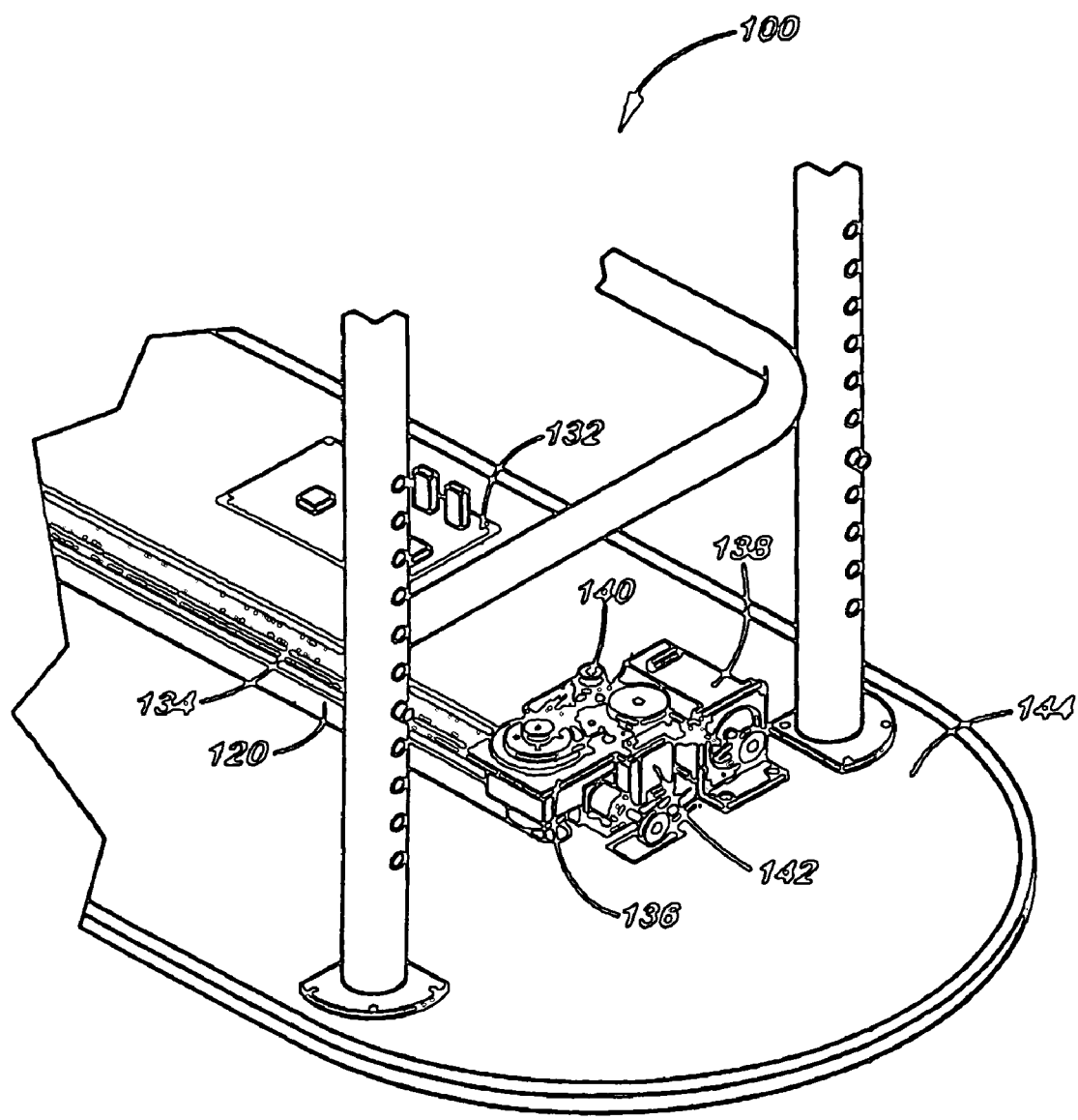
FIG. 7 is a partial isometric view of the drive assembly shown in FIG. 6, further illustrating components of the drive assembly.

FIGS. 6 and 7 further illustrate a drive assembly of automated sampling device 100 attached to a table top bottom. First, FIG. 6 provides an overview of a drive assembly in accordance with the present invention depicting a linear drive 134 running parallel to center slot 120 and connected to sled 128. FIG. 7 is an enlarged view of the drive assembly illustrated in FIG. 6. Drive assembly 100 is comprised of motor one 138, motor two 140, motor three 142, sled 136, linear drive 134, and controller 132. Motor one 138 controls translation of a sample arm assembly's movements along the center slot 120 and is attached to table top bottom 144 and linear drive 134. Any conventional stepper motor known in the art may be used to control translation of the sample arm assembly's movements along center slot 120. Moreover, those of skill in the art will appreciate that any suitable linear drive may be used including a worm drive. Motor two 140 controls angular rotation of a sample arm assembly and is connected to sled 136. In an embodiment, motor two 140 is a radial motor. Motor three 142 controls vertical movement of a sample arm assembly and is attached to sled 136. Any suitable stepper motor may be used for controlling vertical movement of the sample arm assembly. In an additional embodiment, motor three 142 is a slip-clutch system. Further, in accordance with the present invention, the drive assembly may be hard-wired or in the preferred embodiment, controlled via wireless communications. Thus, wireless communications may be utilized to connect controller 132 with the desired analytical instrument (not shown). Utilization of wireless communications allows sample assaying to occur without requiring physical connection with a controller computer increasing mobility of the automated sampling device.

Figure 8:
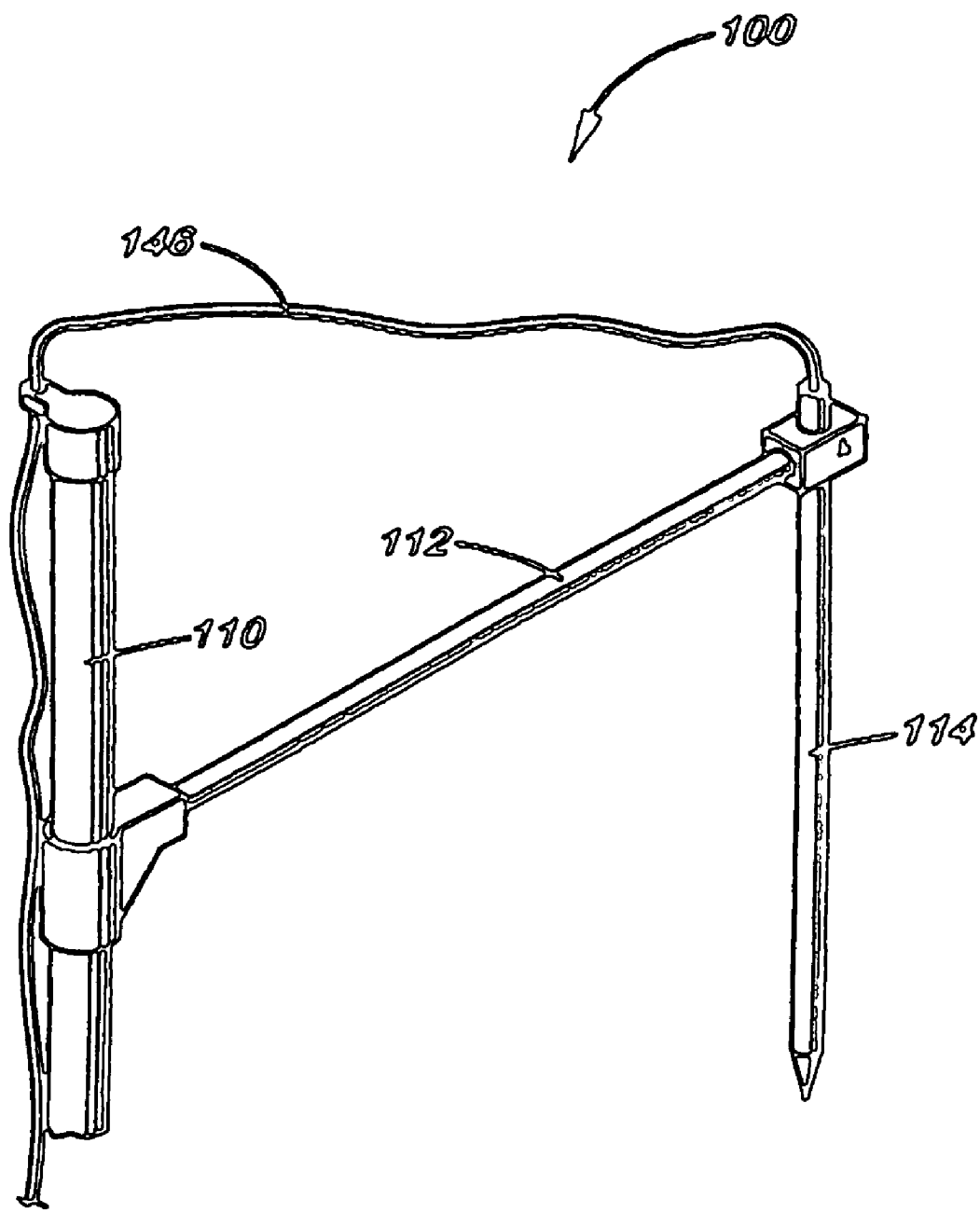
FIG. 8 is a partial isometric view of a sample arm assembly for an automated sampling or dispensing device in accordance with an exemplary embodiment of the present invention.

FIG. 8 provides a detailed depiction of a sample arm assembly of an automated sampling device in accordance with the first exemplary embodiment of the present invention. As previously described, the sample arm assembly includes z-axis support 110 attached to a drive assembly (see FIGS. 6 and 7), sample probe support arm 112 attached to z-axis support 110, and sample probe 114 attached to sample probe support arm 112. In an embodiment, the sample arm assembly is attached to the drive assembly via the z-axis support extending through a center slot in the table top; in such embodiment, the drive assembly is attached to a table top bottom. However, it should be understood to those skilled in the art that the drive assembly may be disposed in a variety of locations including on top of the table top without departing from the scope of the present invention.

In an additional embodiment in accordance with the present invention, sample tubing 146 is present to allow sample removal or reagent delivery as desired. Further, a slip bearing is built into sample probe 114 to prevent winding of sample tubing 146. It is contemplated that the sample may be delivered to various types of scientific instrumentation (e.g. inductively couple plasma system, mass spectrometer) or a number of other types of vessels (e.g. waste collecting bucket following a wash step). It is further contemplated that the sample tubing may be flexible (as shown) or rigid, comprised of plastic, metal, and the like without departing from the scope and spirit of the present invention. In another embodiment, the automated sampling device may be equipped with one or more independent components for the purpose of sample preparation, sample dilution, addition of standards to samples or sample acidification.

Figure 9A:
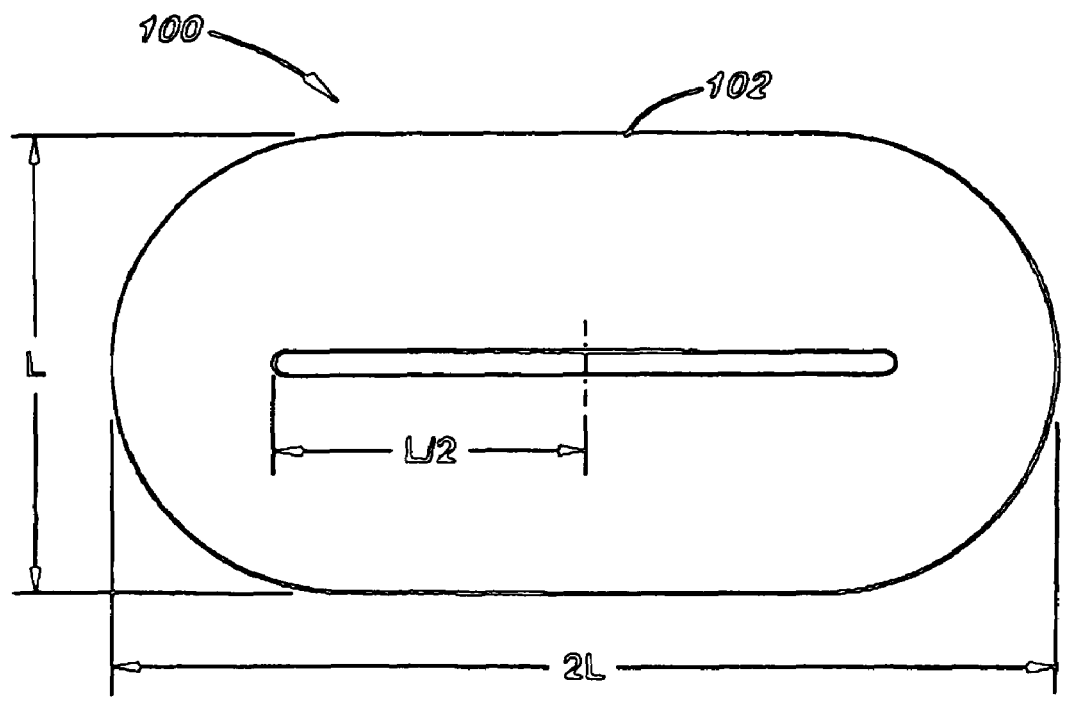
FIG. 9A is plan view illustrating a support surface for use with an automated sampling or dispensing device, wherein the support surface includes a slot and has a footprint in accordance with the first exemplary embodiment of the present invention.
Figure 9B:
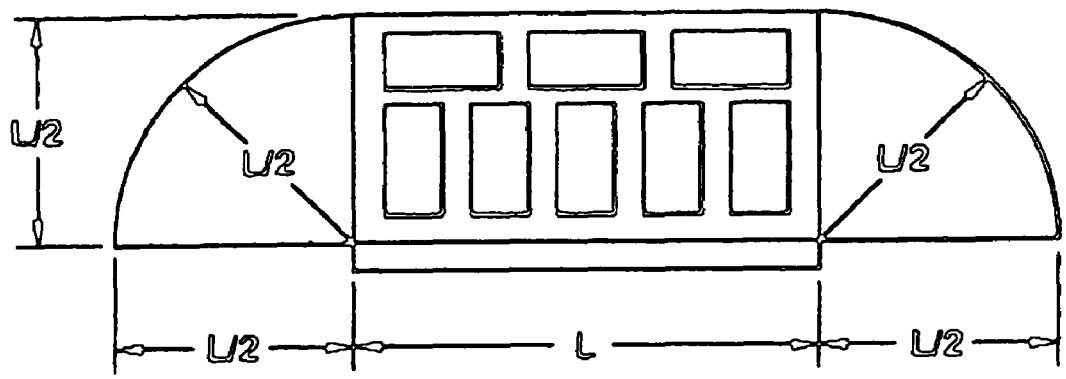
FIG. 9B is plan view illustrating a support surface for use with an automated sampling or dispensing device, in accordance with a fourth exemplary embodiment of the present invention.

Referring to FIGS. 9A and 9B, tables for use with an automated sampling device are described in accordance with exemplary embodiments of the present invention. First, the table 102 includes a slot of length l providing for translation of the sample arm assembly along the length of the table. Further, the table 102 has a footprint for maximizing the usable area of the table 102. As illustrated in FIG. 9A, preferably, the table 102 has a width l substantially equal to the length of the slot l. Moreover, the table 102 is twice as long as the slot, having a length of 2l. Further, the arm length of a sample probe assembly (as shown in FIGS. 1, 2, and 3) is half the length of the slot, having length l/2. This configuration allows for approximately one hundred percent of the footprint of the table to be accessed. In contrast, FIG. 9B illustrates an additional embodiment in accordance with the present invention whereby the table is the shape of a semi-circle and a non-centered slot system is employed.

Figure 10:
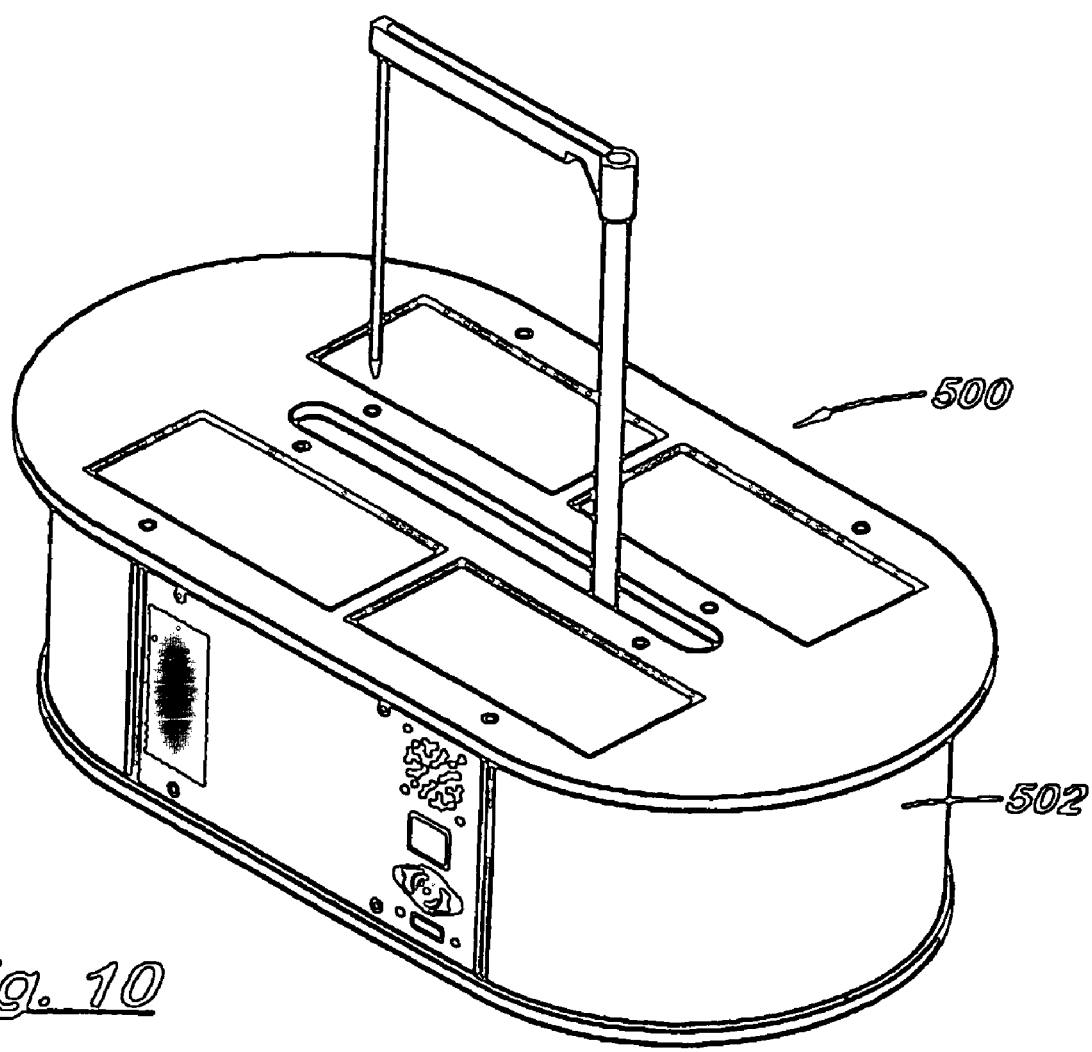
FIG. 10 is an isometric view of an automated sampling or dispensing device in accordance with a fifth exemplary embodiment of the present invention, wherein the device includes a shroud.

Referring to FIG. 10, automated sampling or dispensing device 500 includes a shroud 502. In an exemplary embodiment, the shroud 502 substantially encloses the drive assembly 128 (FIG. 3) for protecting the drive assembly from dust and debris, or preventing dust and debris from the drive assembly from contaminating samples during assaying.

Figure 11:
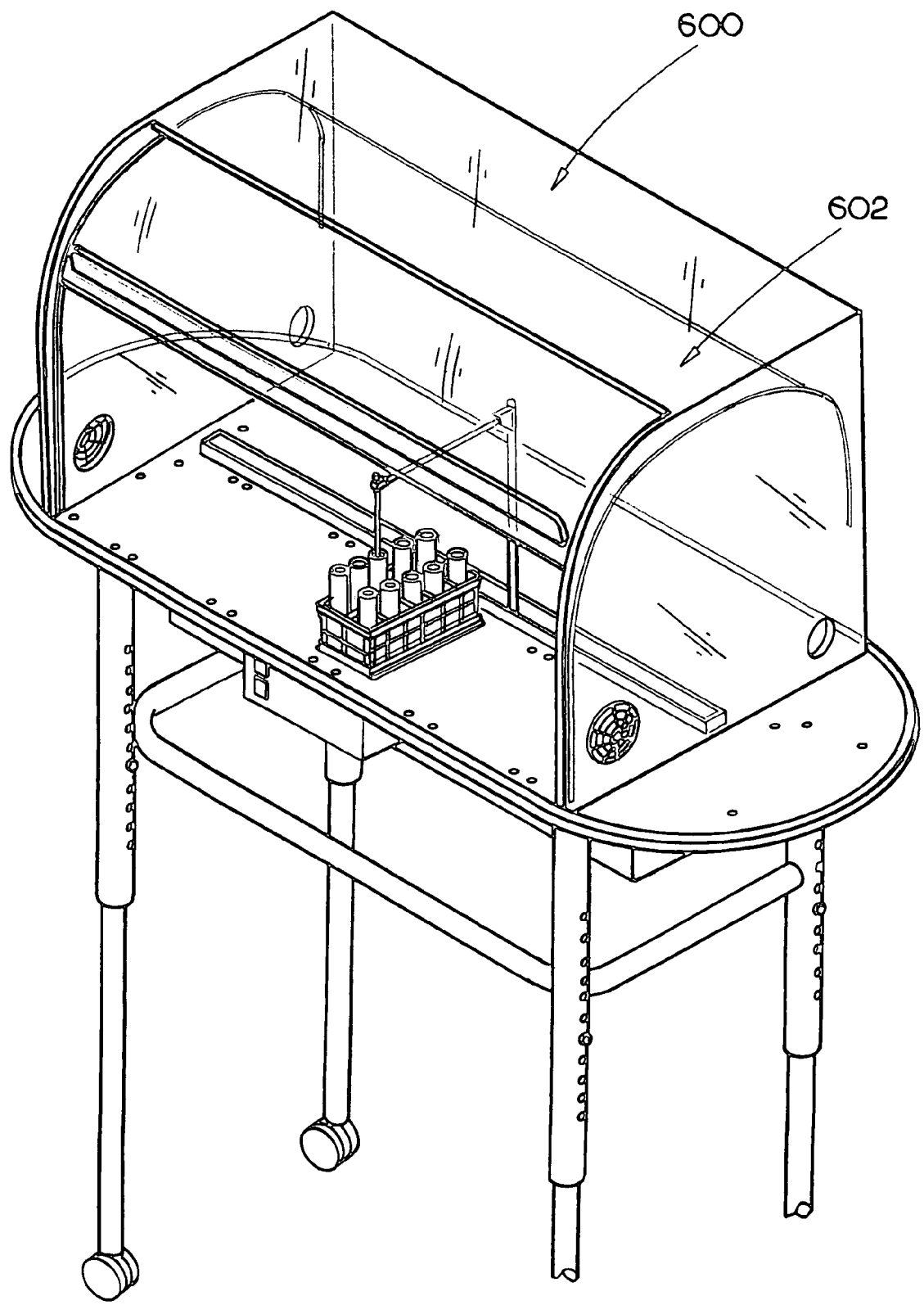
FIG. 11 is an isometric view of an automated sampling or dispensing device in accordance with a sixth exemplary embodiment of the present invention, wherein the device is contained within a hood.

FIG. 11 illustrates automated sampling device 600 completely enclosed within a hood 602. Use of the hood allows the operations inside the hood to be isolated from the outside environment. The area within the hood may be ventilated to prevent the entry of contaminates such as bacteria or air-borne substances. In one specific embodiment, the air drawn into the enclosure is passed through a high efficiency particulate air (HEPA) filter. Further, processing of samples which contain hazardous chemicals within a hood allows such samples to be processed without further exposing the user to such chemicals during processing.

Referring to FIGS. 12 through 19 generally, numerous embodiments of an enclosure for an automated sampling/dispensing device are provided. In general, the enclosure includes at least one support member. The support member is generally perpendicular to a support surface on which the automated sampling/dispensing device is mounted. Further, a lid is mechanically coupled to the at least one support member for covering the support surface on which the automated sampling/dispensing device is mounted. Additionally, at least one flexible sheet is operationally coupled to at least one of the lid or the at least one support member. The at least one support member may provide support to both the lid as well as the at least one flexible sheet. The at least one support member, lid, and at least one flexible sheet enclose the automated sampling device while allowing access to the device by retracting the at least one flexible sheet.

The presently disclosed exemplary enclosures may minimize user exposure to the enclosed samples by allowing the containment of potentially hazardous chemicals within such enclosure. Further, the use of at least one flexible panel allows the enclosure to be shipped efficiently for the enclosure may be disassembled into smaller pieces and thus, be shipped in a smaller box when compared to enclosures with non-flexible panels/doors. Moreover, the use of the at least one flexible panel allows the enclosure to be shaped to accommodate varying shaped automated sampling and or dispensing devices and assemblies.

Figure 12:
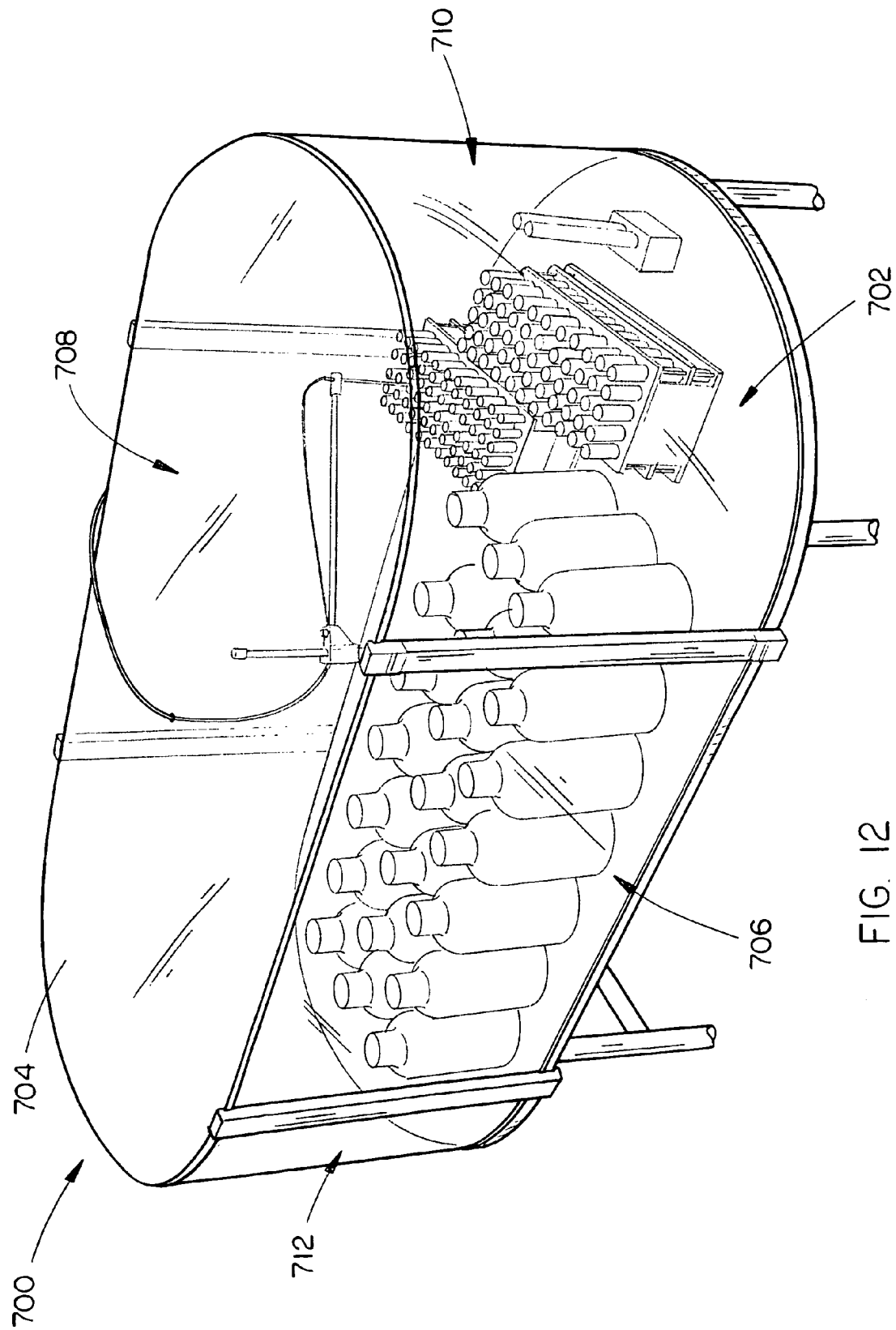
FIG. 12 is an isometric view of an automated sampling or dispensing enclosure in accordance with an exemplary embodiment of the present invention, wherein the enclosure includes two flexible sheets.

Referring specifically to FIG. 12, an enclosure 700 for an automated sampling/dispensing device is provided in which the enclosure 700 surrounds an automated sampling/dispensing device mounted to a circular support surface 702. In an exemplary embodiment, the enclosure 700 includes a lid 704 for covering the support surface 702 on which the automated sampling/dispensing device is mounted. In such embodiment, the lid 704 is generally equivalent in shape and size to that of the support surface 702 allowing the entire support surface 702 to be enclosed and available for use by a user. Further, an aperture for allowing the automated sampling/dispensing device to be connected with devices external to the enclosure may be defined within the lid. As illustrated in FIG. 12, an aperture defined within the lid 704 of the enclosure 700 allows a supply tube to the automated sampling/dispensing device to be connected with an external laboratory analysis equipment. In an alternative embodiment, the enclosure 700 is designed to be airtight allowing the enclosure 700 to contain potentially hazardous chemicals without requiring unnecessary exposure to laboratory personal during sample preparation or analysis.

As illustrated in FIG. 12, the enclosure 700 includes a first support member 706 and a second support member 708. The first 706 and second 708 support members are generally perpendicular to a support surface 702 on which the automated sampling/dispensing device is mounted. For example, as illustrated in FIG. 12, the first support member 706 and the second support member 708 are centered generally one-hundred and eighty degrees opposite from one another. Moreover, such support members may be mechanically coupled to the lid 704 of the enclosure 700 as well as to the support surface 702. For instance, fasteners such as screws, bolts, nuts, and the like may be used to fasten the support members to the lid and support surface. In an advantageous embodiment, all fasteners are either metal-free or coated with an inert plastic coating to prevent interaction of such fasteners with chemical reagents or other substances being used with the automated sampling/dispensing device. In an additional embodiment, an aperture may be formed within one or both of the support members to allow tubes, cords, and the like to be connected to the automated sampling dispensing device contained within the enclosure as well as to external devices (e.g., laboratory analysis equipment), power sources, and the like. It is contemplated that the lid 704 as well as the first support member 706 and the second support member 708 may be formed of inert, light-weight material including Plexiglass® (generically known as the chemical Lucite or polymethyl methacrylate.)

In additional embodiments, as illustrated in FIG. 12, a first flexible sheet 710 and a second flexible sheet 712 are operationally coupled to at least one of the lid 708 or the first support member 706 or the second support member 708. In an embodiment, the first flexible sheet 710 includes a first and second end. The first end of the first flexible sheet 710 includes a finished edge while the second end of the first flexible sheet 710 is fixedly coupled to the second support member 708. For example, the first end of the flexible sheet 710 is finished with a hardened-plastic cover which extends substantially along the length of the first end of the first flexible sheet 710. In addition, at least one guide member is attached to the first end of the first flexible sheet 710 to allow position of the first flexible sheet to be varied.

Figure 13:
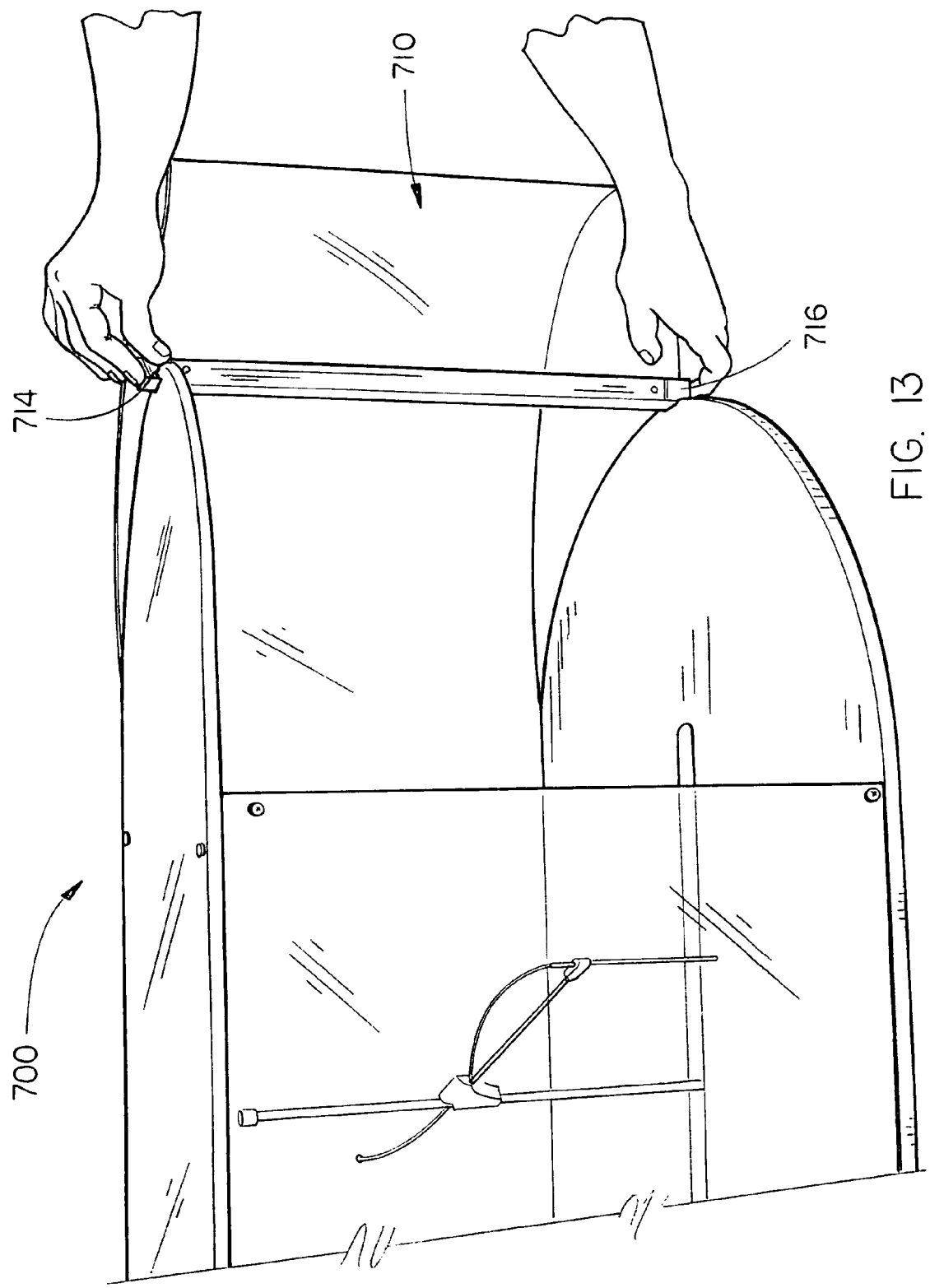
FIG. 13 is a partial front view of the automated sampling or dispensing device enclosure as illustrated in FIG. 12, wherein one of the flexible sheets of the enclosure is retracted.
Figure 14:
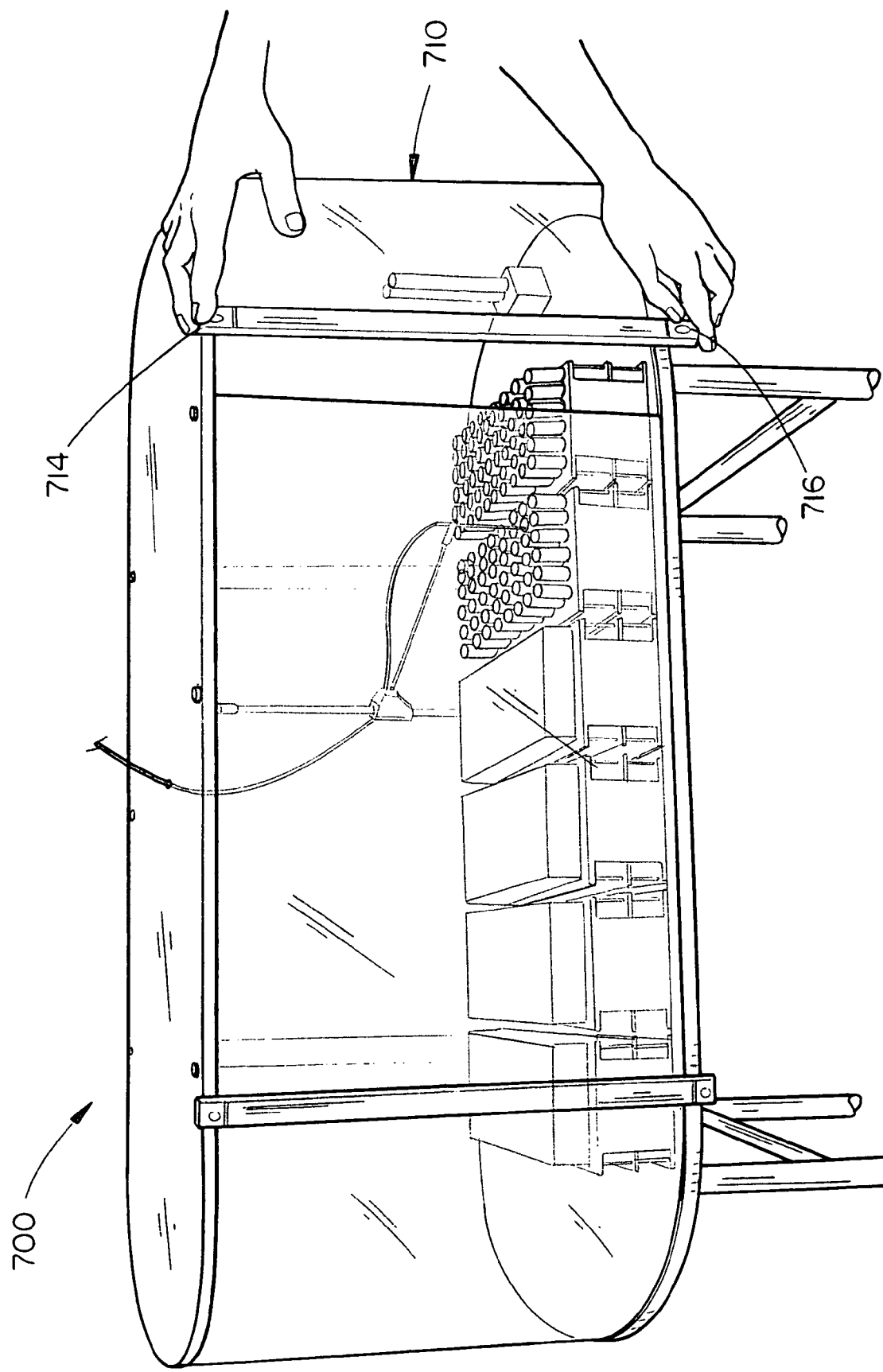
FIG. 14 is a front view of the automated sampling or dispensing device enclosure as illustrated in FIG. 12, wherein the mechanism of fastening a flexible side shut is demonstrated.

As illustrated in FIGS. 13 and 14, the first end of the first flexible sheet 710 includes a first guide member 714 and a second guide member 716 to allow a user to slide the first flexible sheet 710 along an edge of the support surface 702. In an embodiment, the first guide member 714 and the second guide member 716 are press-fit latches allowing a user to secure the flexible sheet at multiple positions along the edge or side of the support surface. For example, a user may release the flexible sheet by applying pressure to the press-fit latches. As illustrated in FIG. 14, a flexible sheet may be moved from a first position to a second position by guiding the first guide member 714 along the edge of the lid 704 while the second guide member is detached from the support surface 710. It is contemplated that additional mechanisms may be employed to guide and secure the flexible sheet at various positions, including fasteners such as clips, pressure-sensitive screws, and the like. It is further contemplated that a channel may be formed within the support surface to provide an area in which a guide member may slide and ultimately, be secured.

In the present embodiment, the second flexible side 712 includes a first and second end. The first end of the second flexible sheet 712 includes a finished edge while the second end of the second flexible sheet 712 is fixedly coupled to the second support member 708. For example, the first end of the second flexible sheet 712 is finished with a hardened-plastic (e.g., plexi-glass) cover which extends substantially along the length of the first end of the second flexible sheet 712. In addition, at least one guide member is attached to the first end of the second flexible sheet 712 to allow position of the first flexible sheet to be varied. For instance, the first end of the second flexible sheet 712 may include a first guide member 714 and a second guide member 716 to allow a user to slide the second flexible sheet 712 along an edge or side of the support surface 702. In an embodiment, the first guide member 714 and the second guide member 716 are press-fit latches allowing a user to secure the flexible sheet at multiple positions along the edge or side of the support surface. It is contemplated that additional mechanisms may be employed to guide and secure the flexible sheet at various positions, including fasteners such as clips, pressure-sensitive screws, and the like.

Figure 15:
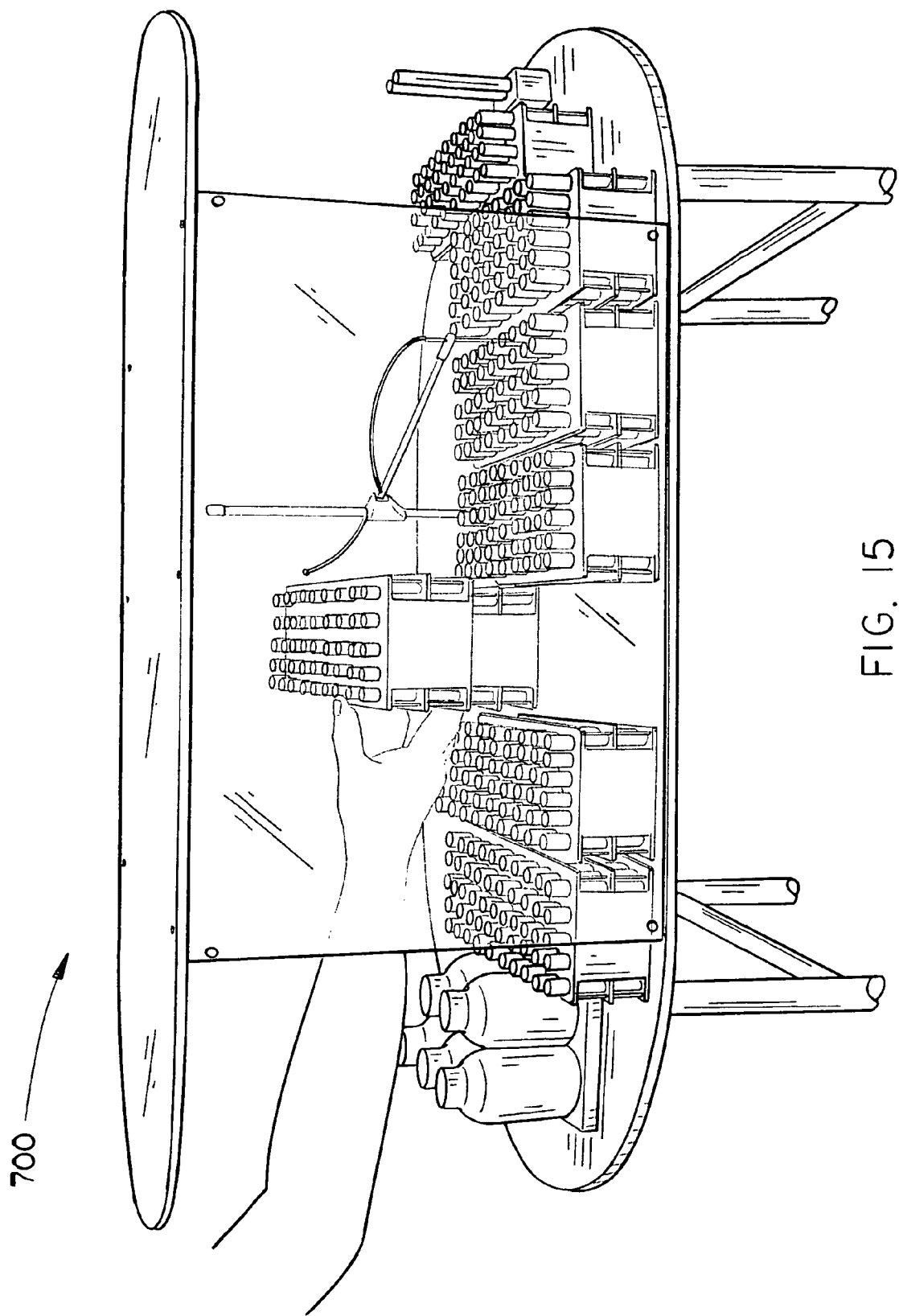
FIG. 15 is a front view of the automated sampling or dispensing device enclosure as illustrated in FIG. 12, wherein the flexible sheets have been removed.

Referring to FIG. 15, the first and second flexible sheets have been removed to allow efficient access to the support surface 702. In an embodiment, the first and second flexible sheets are detachable. The detachable features of such sheets allows a user to load or remove samples efficiently from the support surface 702 in which a user does not have to reposition the sheets in order to gain access to a specific support surface area. It is contemplated that one or both sheets may be removed depending upon the needs of the user.

Figure 16:
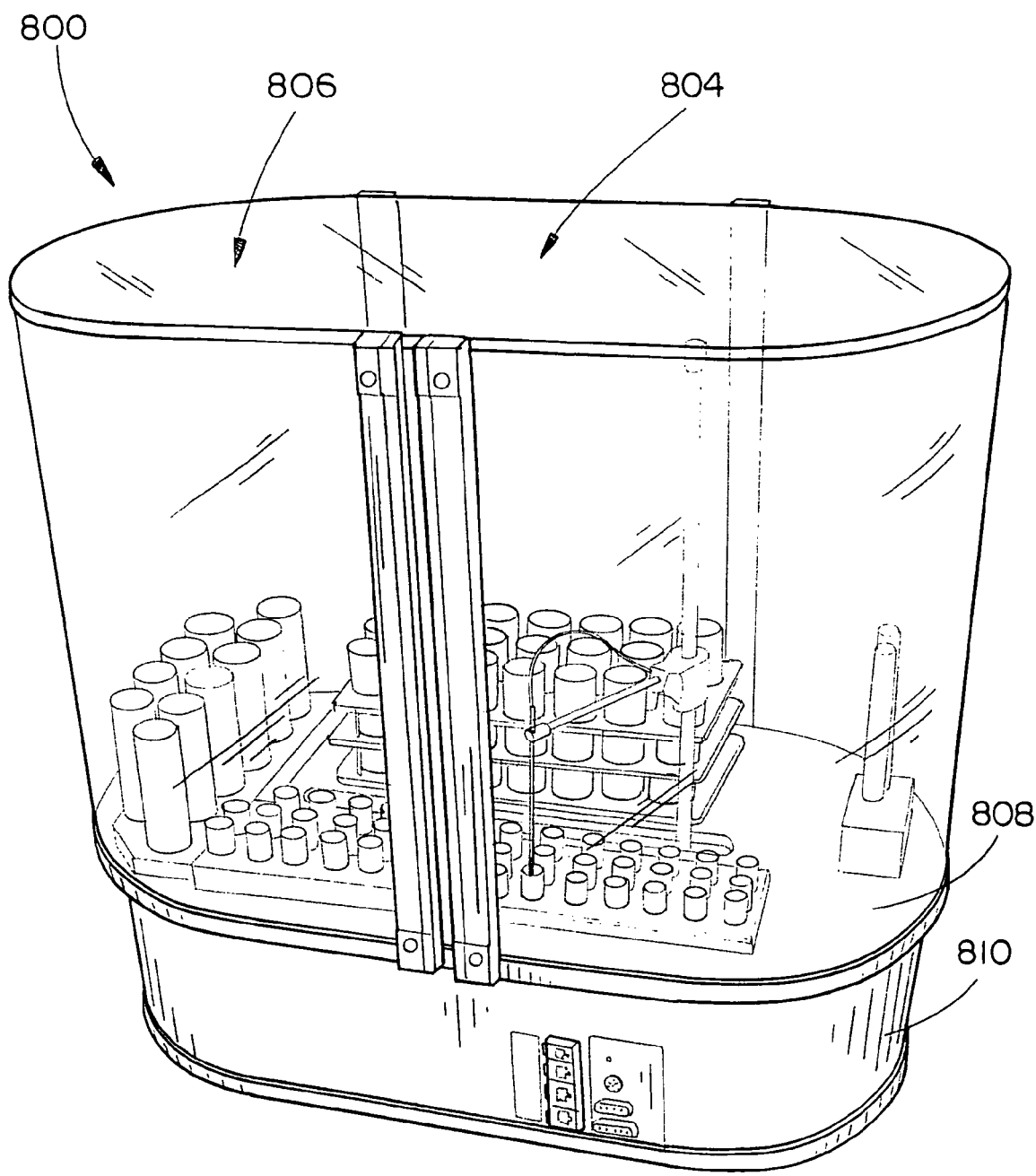
FIG. 16 is an isometric view an enclosure for a bench top automated sampling or dispensing device in accordance with an exemplary embodiment of the present invention, wherein the enclosure includes flexible sheets which are in a closed position.
Figure 17:
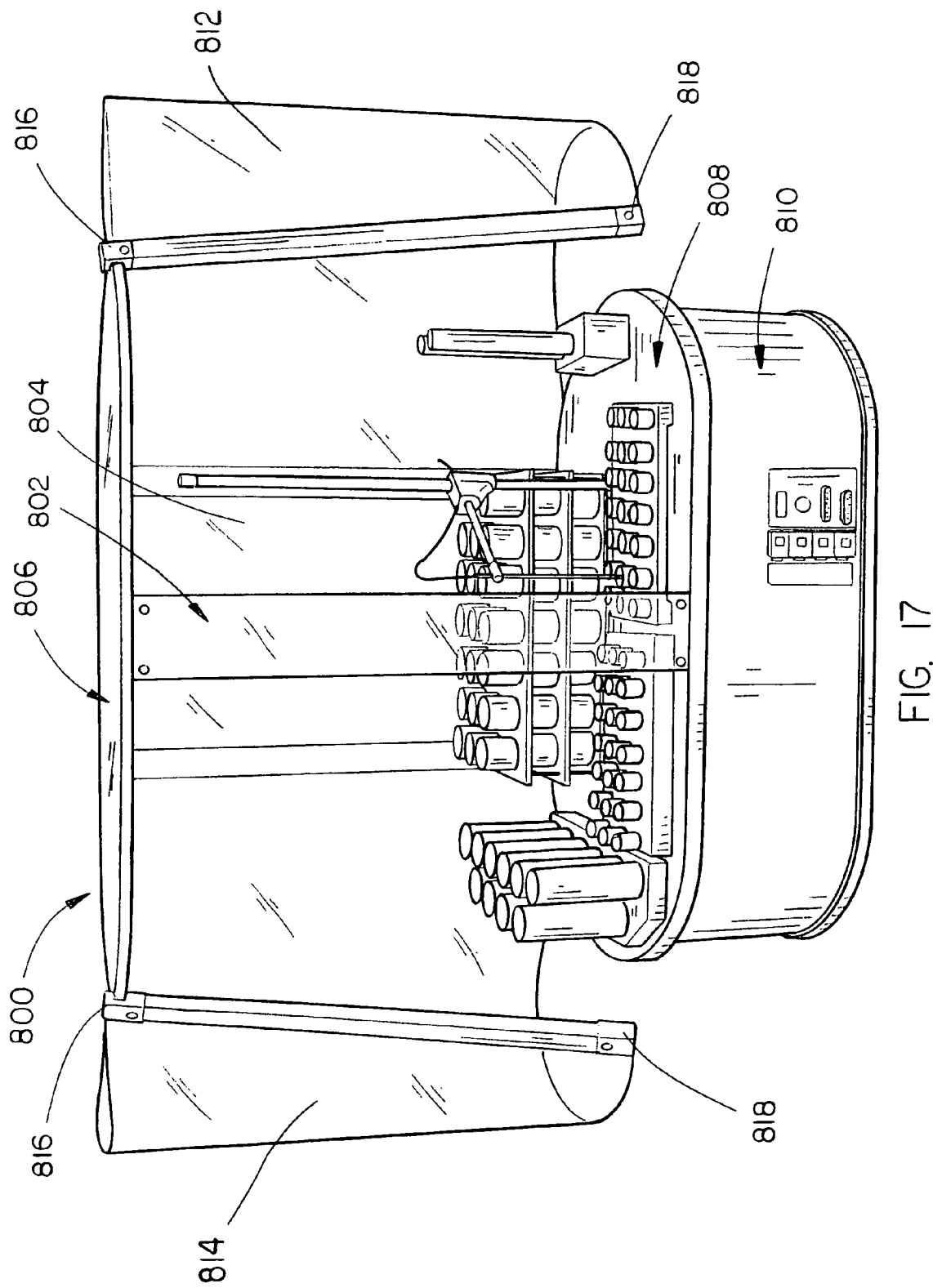
FIG. 17 is a front view of the enclosure for the bench top automated sampling or dispensing device as illustrated in FIG. 16, wherein the flexible sheets are in an open position.

Referring to FIGS. 16 and 17, an additional exemplary enclosure for enclosing an automated sampling/dispensing device is provided in which the automated sampling/dispensing device is a bench-top automated sampling dispensing device. As illustrated in FIGS. 16 and 17, an enclosure 800 for a bench-top automated sampling dispensing device is configured in a similar manner as the enclosure 700 for a table-top automated sampling/dispensing device. The enclosure 800 includes a first support member 802 and a second support member 804 for supporting a lid 806. In an exemplary embodiment, the lid 806 covers a support surface 808 secured to a base 810 of the bench-top automated sampling/dispensing device. In such embodiment, the lid 806 is generally equivalent in shape and size to that of the support surface 808 allowing the entire support surface 808 to be enclosed and available for use by a user. Further, the first 802 and second 804 support members are generally perpendicular to the support surface 808.

As illustrated in FIGS. 16 and 17, the first support member 802 and the second support member 804 are centered generally one-hundred and eighty degrees opposite from one another. For example, the first support member 802 is positioned on the front-side of the automated sampling/dispensing device (the front side being defined as the side including a user power control panel) while the second support member 804 is positioned generally opposite the first support member 802 (e.g., to the rear-side of the automated sampling/dispensing device). Moreover, such support members may be mechanically coupled to the lid 806 of the enclosure 800 as well as to the support surface 808. For instance, fasteners such as screws, bolts, nuts, and the like may be used to fasten the support members to the lid and support surface. In an advantageous embodiment, all fasteners are either metal-free or coated with an inert plastic coating to prevent interaction of such fasteners with chemical reagents or other substances being used with the automated sampling/dispensing device.

It is contemplated that the lid 806 as well as the first support member 802 and the second support member 804 may be formed of inert, light-weight material including Plexiglass® (generically known as the chemical Lucite or polymethyl methacrylate). It is further contemplated that the enclosure 800 may include an aperture within the lid or at least one of the support members allowing for the automated sampling/dispensing device to be connected with devices external to the enclosure. For example, an aperture may be defined within the lid for allowing a supply tube to the automated sampling/dispensing device to be connected with external laboratory analysis equipment. In an alternative embodiment, the enclosure 800 is designed to be airtight allowing the enclosure to contain potentially harmful chemicals without requiring unnecessary exposure to laboratory personal during sample preparation or analysis.

In additional exemplary embodiments, as illustrated in FIG. 17, a first flexible sheet 812 and a second flexible sheet 814 are operationally coupled to at least one of the lid 806 or the first support member 802 or the second support member 804. In an embodiment, each flexible sheet includes a first and second end. The first end of each flexible sheet includes a finished edge while the second end of each flexible sheet is fixedly coupled to the second support member 804. For example, the first end of the flexible sheet 812 is finished with a hardened-plastic cover (e.g., Plexiglass®) which extends substantially along the length of the first end of the first flexible sheet 812.

In further exemplary embodiments, at least one guide member is attached to the first end of each flexible sheet to allow the position of each flexible sheet to be varied. As illustrated in FIG. 17, the first end of each flexible sheet includes a first guide member 816 and a second guide member 818 to allow a user to slide each sheet along an edge of the lid 806 or support surface 808. In an embodiment, the first guide member 816 and the second guide member 818 are press-fit latches allowing a user to secure the flexible sheet at multiple positions along the edge or side of the lid or support surface. For example, a user may release the flexible sheet by applying pressure to the press-fit latches. As illustrated in FIG. 17, a flexible sheet may be moved from a first position to a second position by guiding the first guide member 816 along the edge of the lid 806 while the second guide member 818 is detached from the support surface 808. It is contemplated that additional mechanisms may be employed to guide and secure the flexible sheet at various positions, including fasteners such as clips, pressure-sensitive screws, and the like. It is further contemplated that a channel may be formed within the support surface to provide an area in which a guide member may slide and ultimately, be secured.

It is contemplated that the first and second flexible sheets may be detachable. The detachable features of such sheets allows a user to load or remove samples efficiently from the support surface 808 in which a user does not have to reposition the sheets in order to gain access to a specific support surface area. It is contemplated that one or both sheets may be removed depending upon the needs of the user.

Figure 18:
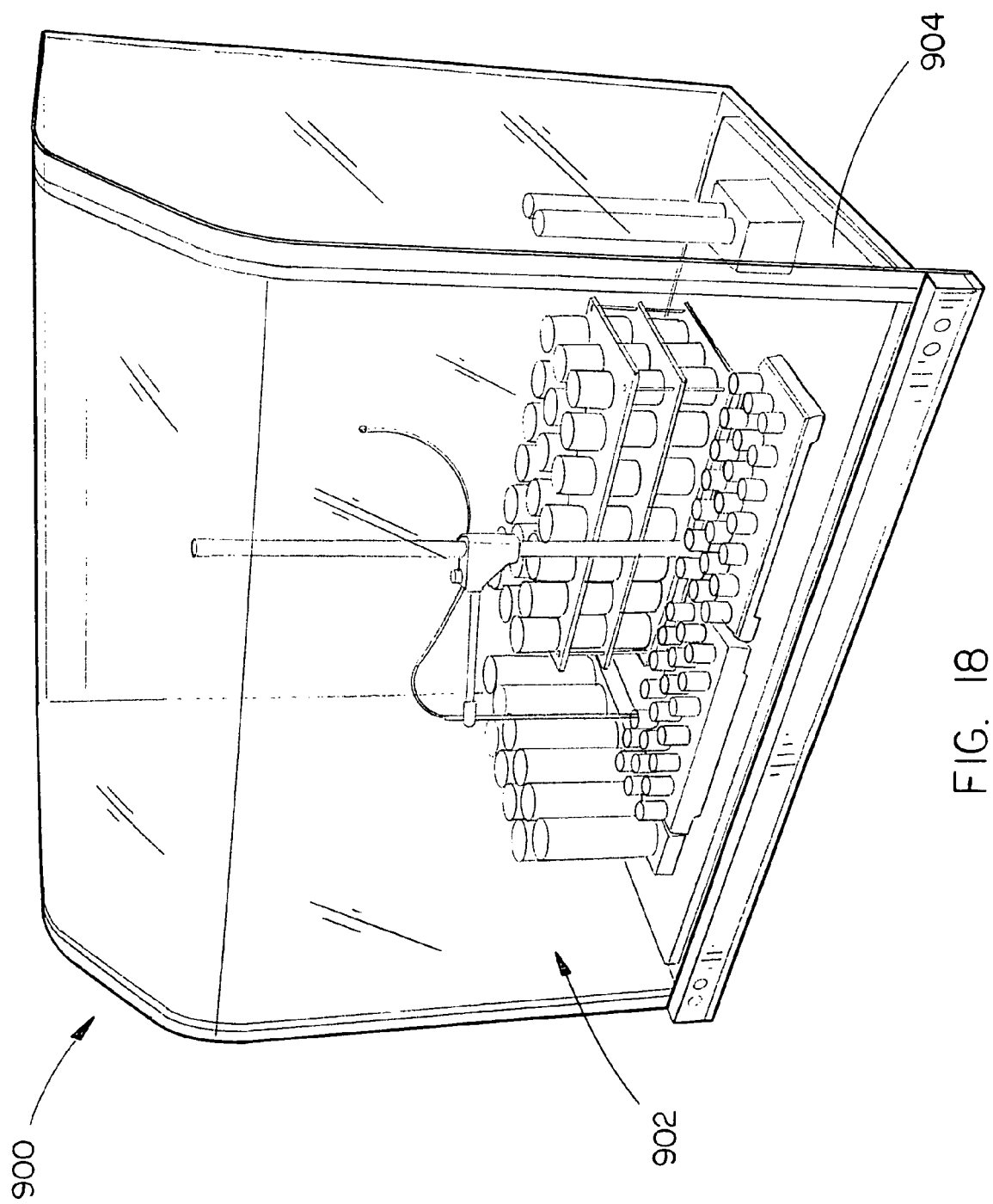
FIG. 18 is an isometric view of an enclosure for an automated sampling or dispensing device in accordance with an additional exemplary embodiment of the present invention, wherein the enclosure includes a single flexible front sheet.
Figure 19:
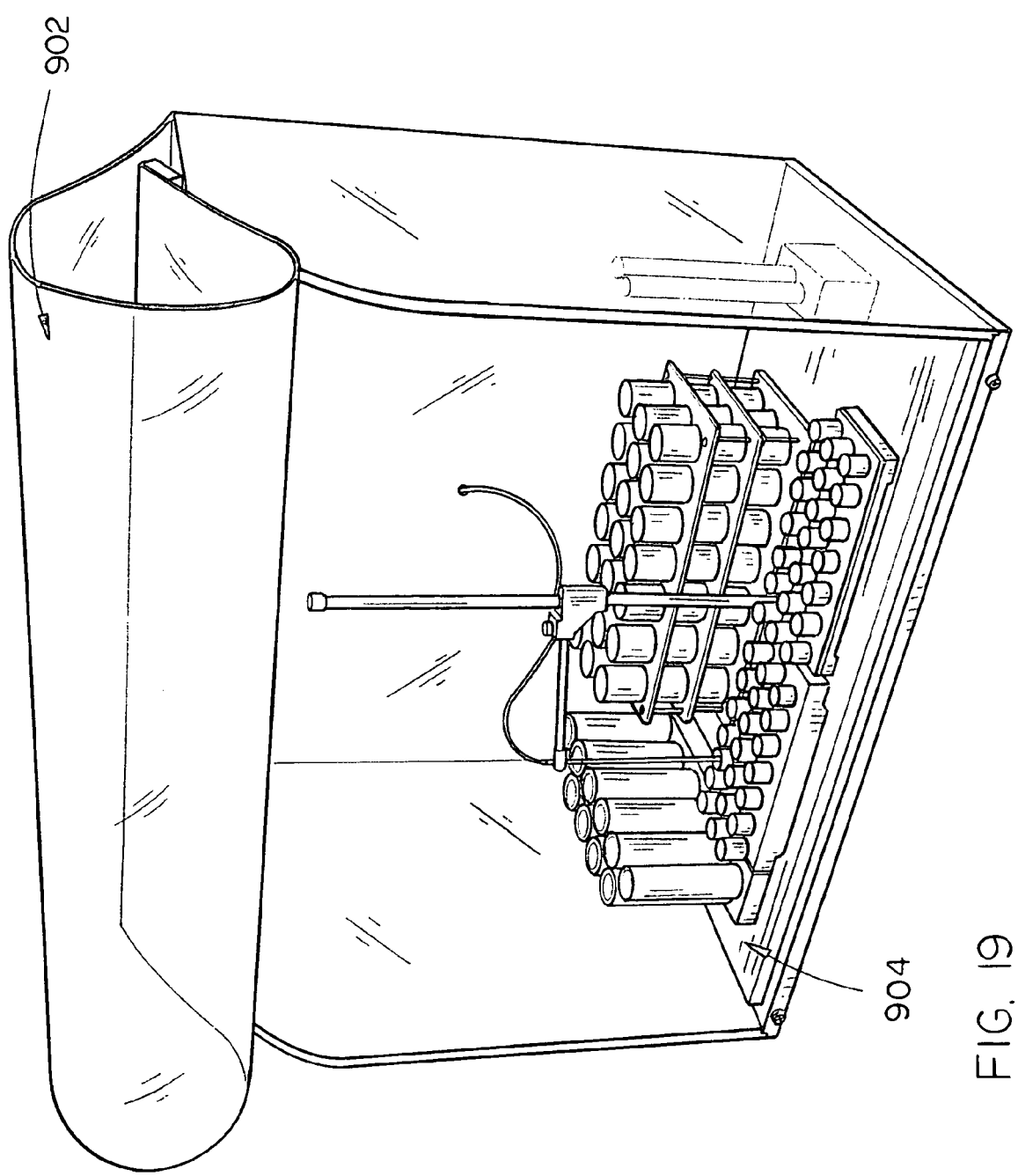
FIG. 19 is an isometric view of the enclosure for the automated sampling or dispensing device as illustrated in FIG. 18, wherein the front sheet is retracted allowing access to the device.

Referring to FIGS. 18 and 19, a further exemplary enclosure 900 for enclosing an automated sampling/dispensing device is provided in which the enclosure 900 includes a single flexible sheet or panel 902. As illustrated in FIGS. 18 and 19, the enclosure 900 includes a plurality of support walls and a single flexible sheet 902 for enclosing the automated sampling/dispensing device mounted on a support surface 904. For example, the enclosure 900 may include three support walls and the single flexible sheet 902. In such example, a first side support wall and a second side support wall provide support to a rear support wall in which the rear support wall is secured to an edge of the first side support wall and an edge of the second side support wall. The rear support wall is generally opposite to that of the front of the enclosure. Further, the front of the enclosure being that which includes the flexible sheet and is utilized by a user to gain access to the automated sampling/dispensing device. The first and second side support walls are configured to allow the flexible sheet to be rolled along an outer edge of the first side support wall and an outer edge of the second side support wall. It is contemplated that an aperture may be defined within at least one of the plurality of walls for allowing the enclosed apparatus to be connected with external devices or power sources.

With continued reference to FIGS. 18 and 19, the single flexible sheet 902 includes a first and second edge. The first end of the flexible sheet 902 includes a finished edge while the second end of the flexible sheet 902 is fixedly coupled to the rear support wall. For example, the first end of the flexible sheet 902 is finished with a hardened-plastic cover which extends substantially along the length of the first end of the flexible sheet 902. To gain access to the interior of the enclosure 900, the single flexible sheet 902 may be retracted with a first end of the first edge of the single flexible sheet 902 being secured to the outer edge of the first side support wall and a second end of the first edge being secured to the outer edge of the second side support wall. It is contemplated that various mechanisms may be employed to secure the first edge of the flexible sheet 902 to the side support edges including press fit latches, clips, screws, and the like. In addition, the enclosure 900 may be mounted to an automated sampling/dispensing device which is integral to laboratory analysis equipment in which the enclosure may positioned to enclose such device by securing the enclosure to a support area supporting the device. Moreover, the single flexible sheet may be detachable allowing a user access to the entire support surface area as well as to the over-head support surface area.

Although the presently disclosed enclosure focuses upon the use of such enclosure with an automated sampling/dispensing device, it is contemplated that such enclosure may be employed with a variety of types of laboratory equipment without departing from the scope and spirit of the present invention. It is further contemplated that the aforementioned exemplary enclosures may be ventilated with may be ventilated to prevent the entry of contaminates such as bacteria or air-borne substances into the external environment. For instance, the air drawn into the enclosure is passed through a HEPA filter.

Figure 20:
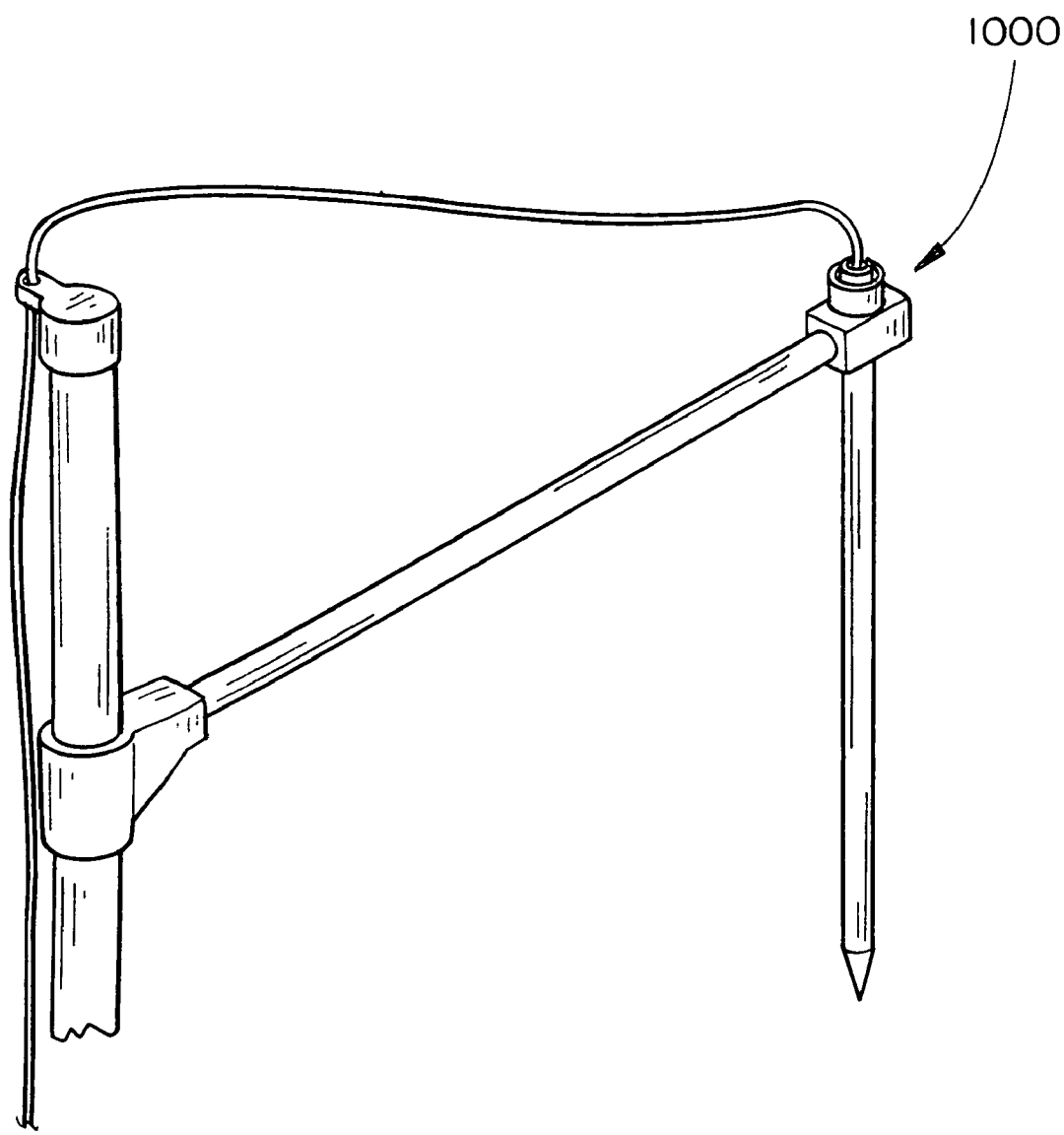
FIG. 20 is a partial isometric view of a sample arm assembly for an automated sampling or dispensing device in accordance with an exemplary embodiment of the present invention, wherein the sample arm assembly includes a dampening device for dampening vibrations generated during use.

Referring now to FIG. 20, a sample arm assembly for an automated sampling or dispensing device in accordance with an exemplary embodiment of the present invention is provided in which the sample arm assembly includes a dampening device for dampening vibrations generated during use. As illustrated in FIG. 20, the sample arm assembly includes the sample probe 114 allowing samples to be dispensed or removed from various sample vessels. A dampening device 1000 is positioned around a first end of the sample probe 114 which is generally opposite to a second end of the sample probe 114, the second end of the sample probe making contact with sample and sample vessels. The dampening device 1000 allows the vibrations generated during operation of the automated sampling/dispensing device to be minimized by moving out of phase with the automated sampling/dispensing device sample probe. The minimization of the vibrations allows accurate positioning of the sample probe and thus, minimizes the possibility of sample cross-contamination without requiring the speed of the automated sampling/dispensing device to be reduced.

Figure 21:
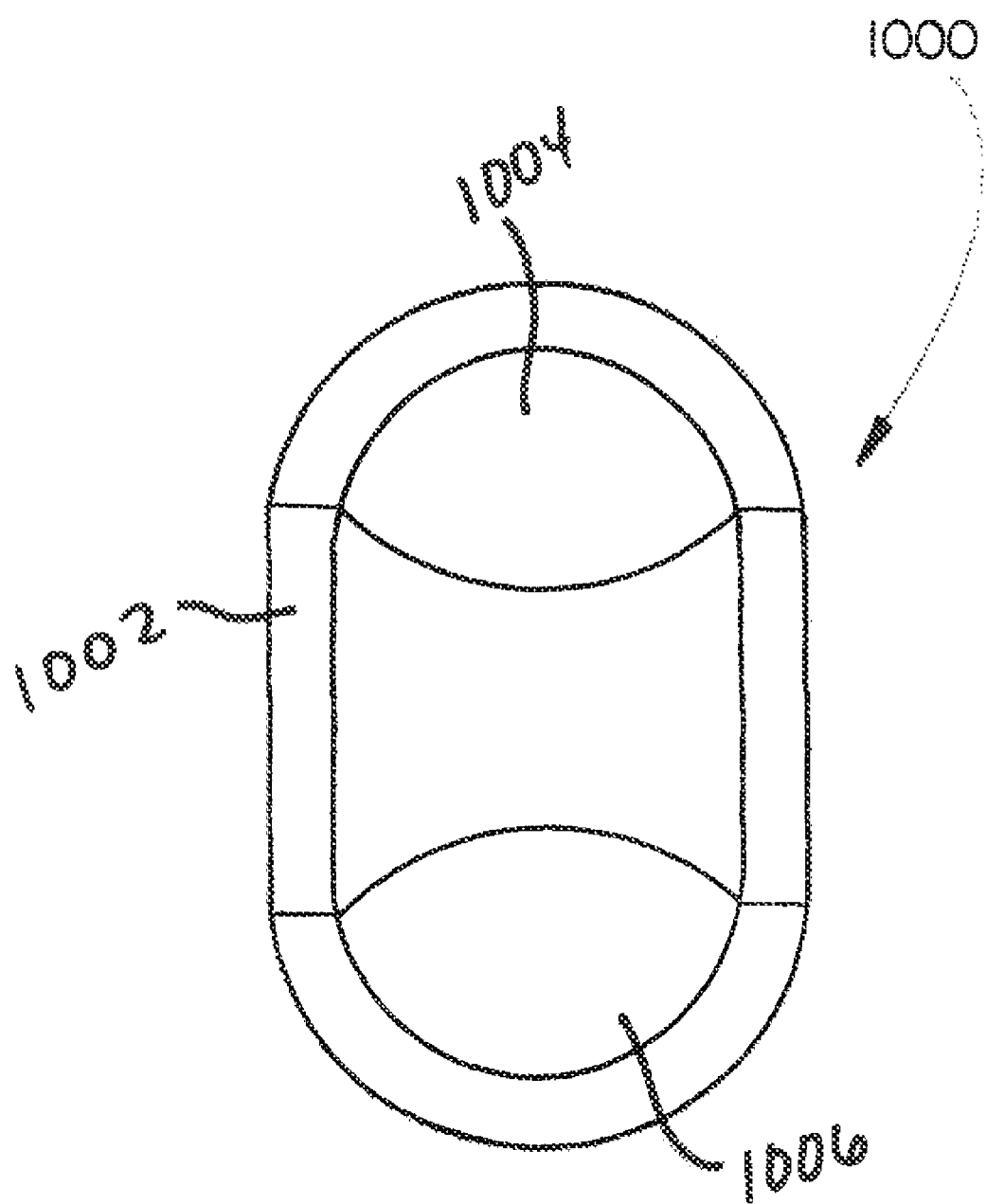
FIG. 21 is an isometric view of a dampening device for an automated sampling or dispensing device in accordance with an exemplary embodiment of the present invention.

In an exemplary embodiment, the dampening device 1000 includes a body 1002 with a plurality of walls. As illustrated in FIG. 21, the body 1002 is generally cylindrical and includes a first end and a second end. Further, a first opening 1004 is defined within the first end and a second opening 1006 is defined within the second end. Further, in an embodiment, the body 1002 includes an inner diameter greater than an outer diameter of an automated sampling/dispensing device sample probe. For example, for a sample probe with a diameter of 3 millimeters, the inner diameter of the cylindrical body is approximately 6 millimeters. The use of a dampening device with an inner cylindrical diameter approximately two times that of the sample probe allows the device to be placed loosely around the first end of the sample probe. During operation, the dampening device is allowed to move out of phase with the automated sampling/dispensing device sample probe allowing sample probe vibrations to be dampened.

Figure 22B:
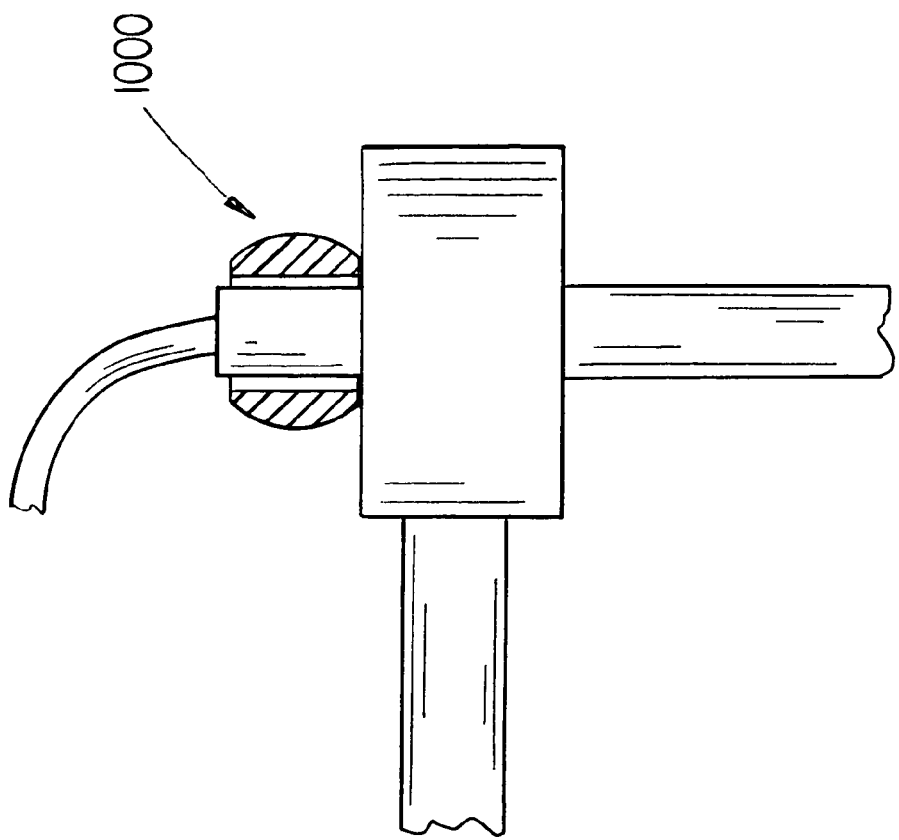
FIG. 22B is a partial side view of an automated sampling or dispensing device in accordance with an exemplary embodiment of the present invention, wherein a cross-sectional view of an additional exemplary dampening device is provided.
Figure 22A:
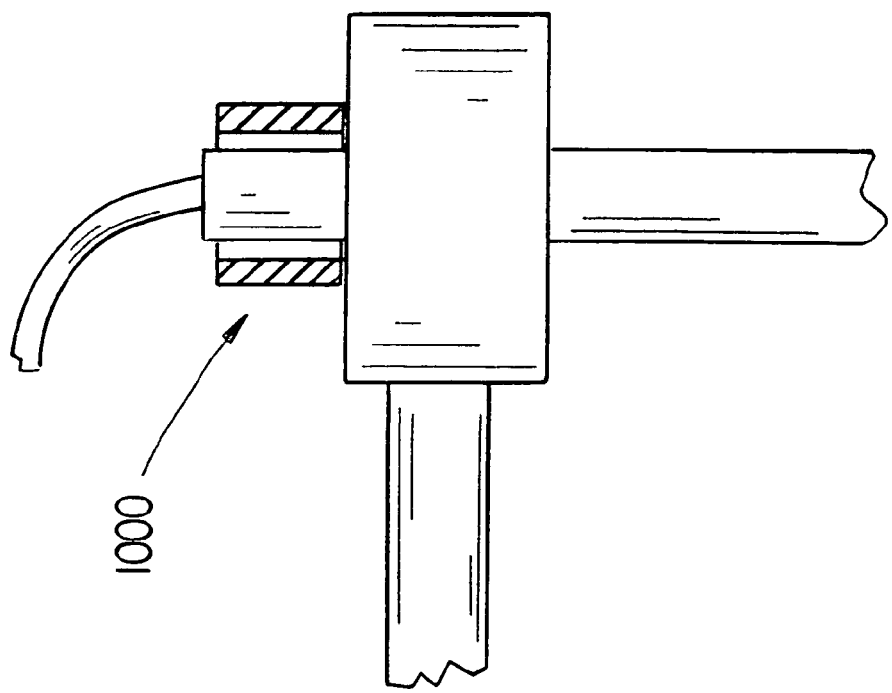
FIG. 22A is a partial side view of an automated sampling or dispensing device in accordance with an exemplary embodiment of the present invention, wherein a cross-sectional view of an exemplary dampening device is provided.

It is contemplated that the dampening device may be composed of metal-free, inert material including plastic. The use of metal-free, inert materials allows the dampening device to be lightweight and removes the possibility of the device reacting with any chemicals or other substance. It is further contemplated that the size and shape of the dampening device may vary depending upon the size and shape of the sample probe on which it is to be positioned. For example, as illustrated in FIGS. 22A and 22B, the inner diameter of the dampening device may be square or spherical, respectively.

In an additional exemplary embodiment, the body 1002 of the dampening device 1000 includes a slit extending along the length of the cylindrical body for allowing the dampening device 1000 to be positioned around the first end of the sample probe 114 which is generally opposite to the second end of the sample probe 114 which makes contact with a sample. The slit allows the dampening device 1000 to be positioned without requiring the user to slide the device over additional components of the automated sampling/dispensing device. For example, the slit is of a width to allow the dampening device 1000 to be positioned around the first end of the sample probe 114 and remain around the first end of the sample probe 114 during sample probe operation.

It is believed that the present invention and many of its attendant advantages will be understood by the foregoing description. It is also believed that it will be apparent that various changes may be made in size, materials, shape, form, function, manner of operation, assembly and use of the components thereof without departing from the scope and spirit of the invention or without sacrificing all of its material advantages. The form herein before described being merely an explanatory embodiment thereof. Further, it is contemplated that the specific order or hierarchy of steps in the method can be rearranged while remaining within the scope and spirit of the present invention. It is the intention of the following claims to encompass and include such changes.

What is claimed is:

1. A dampening device for an automated sampling and dispensing device, comprising:
   a cylindrical body, the cylindrical body including a first end and a second end, a first opening being defined within the first end and a second opening being defined within the second end allowing the cylindrical body to be positioned around an automated sampling and dispensing device sample probe; the cylindrical body including an inner diameter greater than an outer diameter of the automated sampling and dispensing device sample probe, the inner diameter of the cylindrical body partially contacting the outer diameter of the automated sampling and dispensing device,
   the cylindrical body moving out of phase with the automated sampling/dispensing device sample probe allowing sample probe vibrations to be dampened during operation.

2. The dampening device as claimed in claim 1, wherein the dampening device is positioned around a first end of the sample probe which is generally opposite to a second end of the sample probe which makes contact with a sample.

3. The dampening device as claimed in claim 1, wherein the dampening device is formed of plastic.

4. The dampening device as claimed in claim 1, wherein the dampening device is formed of metal-free material.

5. A dampening device for an automated sampling/dispensing device, comprising:
   a body, the body including a plurality of walls, a first end and a second end, a first opening being defined within the first end and a second opening being defined within the second end allowing the cylindrical body to be positioned around an automated sampling and dispensing device sample probe; the body including an inner diameter greater than an outer diameter of an automated sampling and dispensing device sample probe, the inner diameter of the body partially contacting the outer diameter of the automated sampling and dispensing device,
   wherein the dampening device is positioned around the automated sampling and dispensing device sample probe so that during operation the device moves out of phase with the automated sampling/dispensing device sample probe allowing sample probe vibrations to be dampened.

6. The dampening device as claimed in claim 5, wherein the dampening device is positioned around a first end of the sample probe which is generally opposite to a second end of the sample probe which makes contact with a sample.

7. The dampening device as claimed in claim 5, wherein the plurality of walls are configured to form a cylindrical body.

8. The dampening device as claimed in claim 5, wherein the inner diameter of the body is cylindrical in shape.

9. The dampening device as claimed in claim 5, wherein the dampening device is formed of plastic.

10. The dampening device as claimed in claim 5, wherein the dampening device is formed of metal-free material.

11. An automated sampling and dispensing device including a dampening device, comprising:
    a support surface for supporting a sample holder, the sample holder being suitable for holding a sample vessel;
    a sample arm assembly for supporting a sample probe, the sample arm assembly including a z-axis support and a sample probe support arm;
    a drive assembly coupled to the z-axis support of the sample arm assembly for powering and positioning the sample arm assembly, the drive assembly causes the sample arm assembly to move in translation along the x-axis, in translation along an axis coaxial with the z-axis support, and radially about the z-axis; and
    a dampening device operationally coupled to the sample arm assembly for dampening vibrations of the sample arm assembly during operation, the dampening device including a cylindrical body, the cylindrical body including a first end and a second end, a first opening being defined within the first end and a second opening being defined within the second end allowing the cylindrical body to be positioned around the sample probe; the cylindrical body including an inner diameter greater than an outer diameter of the sample probe, the inner diameter of the cylindrical body partially contacting the outer diameter of the automated sampling and dispensing device, wherein the dampening device is positioned around the sample probe so that during operation the dampening device moves out of phase with the sample probe allowing sample probe vibrations to be dampened.

12. The automated sampling and dispending device including a dampening device as claimed in claim 11, wherein the dampening device is positioned around a first end of the sample probe which is generally opposite to a second end of the sample probe which makes contact with the sample vessel.

13. The automated sampling and dispending device including a dampening device as claimed in claim 11, wherein the dampening device is formed of plastic.

* * * * *